(12) United States Patent
Anand

(10) Patent No.: US 11,234,947 B2
(45) Date of Patent: Feb. 1, 2022

(54) TREATMENT OF PERIPHERAL NEUROPATHY INDUCED BY CANCER CHEMOTHERAPY

(71) Applicant: IMPERIAL COLLEGE INNOVATIONS LIMITED, London (GB)

(72) Inventor: Praveen Anand, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 0 days.

(21) Appl. No.: 16/916,182

(22) Filed: Jun. 30, 2020

(65) Prior Publication Data

US 2021/0401780 A1 Dec. 30, 2021

(51) Int. Cl.
| | | |
|---|---|---|
| *A61K 31/165* | (2006.01) | |
| *A61P 25/02* | (2006.01) | |
| *A61K 9/70* | (2006.01) | |
| *A61K 9/00* | (2006.01) | |

(52) U.S. Cl.
CPC .......... *A61K 31/165* (2013.01); *A61K 9/7023* (2013.01); *A61P 25/02* (2018.01); *A61K 9/0014* (2013.01)

(58) Field of Classification Search
CPC .................................................. A61K 31/165
See application file for complete search history.

(56) References Cited

U.S. PATENT DOCUMENTS

| | | | | |
|---|---|---|---|---|
| 6,239,180 B1* | 5/2001 | Robbins | ............... | A61K 31/485 |
| | | | | 514/627 |
| 2004/0101582 A1* | 5/2004 | Wolicki | ............... | A61K 31/455 |
| | | | | 424/760 |
| 2004/0202707 A1* | 10/2004 | Muller | ................... | A61P 25/02 |
| | | | | 424/449 |
| 2014/0303203 A1* | 10/2014 | Hoke | ................... | C07D 215/48 |
| | | | | 514/311 |

OTHER PUBLICATIONS

Abooj et al, "Changes in Spinal Cord Following Inflammatory and Neuropathic Pain and the Effectiveness of Resiniferatoxin," The Open Pain Journal, 2016, vol. 9, pp. 1-14.

Anand et al, "Topical capsaicin for pain management: therapeutic potential and mechanisms of action of the new high-concentration capsaicin 8% patch," British Journal of Anaesthesia, 2011, vol. 107, No. 4, pp. 490-502.

(Continued)

*Primary Examiner* — Benjamin J Packard
(74) *Attorney, Agent, or Firm* — Kilyk & Bowersox, P.L.L.C.

(57) ABSTRACT

Methods of treating peripheral neuropathy induced by cancer chemotherapy and/or of stimulating the regeneration of peripheral sensory nerve fibers, comprising administering topically to one or more areas of the skin capsaicin or a capsaicinoid or topical TRPV1 agonist, to a patient in need thereof, wherein the capsaicin or capsaicinoid or TRPV1 agonist is administered after the patient has received cancer chemotherapy, and wherein the patient is not currently receiving cancer chemotherapy. Related kits comprising capsaicin-containing cutaneous patches for use with said methods.

20 Claims, 8 Drawing Sheets

(56) References Cited

OTHER PUBLICATIONS

Anand et al, "Rational treatment of chemotherapy-induced peripheral neuropathy with capsaicin 8% patch: from pain relief towards disease modification," Journal of Pain Research, 2019, vol. 12, pp. 2039-2052.
Filipczak-Bryniarska et al, "High-dose 8% capsaicin patch in treatment of chemotherapy-induced peripheral neuropathy: single-center experience," Med Oncol, 2017, 34:162 (5 pages).
Kennedy et al, "A Randomized, Controlled, Open-Label Study of the Long-Term Effects of NGX-4010, a High-Concentration Capsaicin Patch, on Epidermal Nerve Fiber Density and Sensory Function in Healthy Volunteers," The Journal of Pain, Jun. 2010, vol. 11, No. 6, pp. 579-587.
Khoshnoodi et al, "Effect of diabetes type on long-term outcome of epidermal axon regeneration," Annals of Clinical and Translational Neurology, 2019, vol. 6, No. 10, pp. 2088-2096.
Le Marec et al, "Improvement of chemotherapy induced neuropathy (CIN) in cancer patients using capsaicin 8% patch," Journal of Clinical Oncology, 2016, vol. 34, No. 15 Suppl (4 pages).
Polydefkis et al, "The time course of epidermal nerve fibre regeneration: studies in normal controls and in people with diabetes, with and without neruopathy," Brain, 2004, vol. 127, No. 7, pp. 1606-1615.
Privitera et al, "Capsaicin 8% patch treatment for amputation stump and phantom limb pain: a clinical and functional MRI study," Journal of Pain Research, 2017, vol. 10, pp. 1623-1634.
Rage et al, "The time course of CO2 laser-evoked responses and of skin nerve fibre markers after topical capsaicin in human volunteers," Clinical Neurophysiology, 2010, vol. 121, pp. 1256-1266.
Webster et al, "Tolerability of NGX-4010, a capsaicin 8% dermal patch, following pretreatment with lidocaine 2.5%/prilocaine 2.5% cream in patients with post-herpetic neuralgia," BMC Anesthesiology, 2011, vol. 11, No. 25 (8 pages).
Anand et al, "The role of endogenous nerve growth factor in human diabetic neuropathy," Nature Medicine, Jun. 1996, vol. 2, No. 6, pp. 703-707.
Anand et al, "Endogenous NGF and CNTF levels in human peripheral nerve injury," NeuroReport, May 27, 1997, vol. 8, No. 8, pp. 1935-1938.
Anand, "Neurotrophic factors and their receptors in human sensory neuropathies," Progress in Brain Research, 2004, vol. 146, pp. 478-492.
Anand et al, "Trench Foot or Non-Freezing Cold Injury As a Painful Vaso-Neuropathy:Clinical and Skin Biopsy Assessments," Frontiers in Neurology, Sep. 2017, vol. 8, Article 514, pp. 1-16.
Apostolidis et al, "Capsaicin Receptor TRPV1 in Urothelium of Neurogenic Human Bladders and Effect of Intravesical Resiniferatoxin," Basic Science, 2005, Urology 65, pp. 400-405.
Atherton et al, "Use of the novel contact heat evoked potential stimulator (CHEPS) for the assessment of small fibre neuropathy: correlations with skin flare responses and intra-epidermal nerve fibre counts," BMC Neurology 2007, vol. 7, No. 21 (10 pages).
Bakitas, "Background Noise—The Experience of Chemotherapy-Induced Peripheral Neuropathy," Nursing Research, Sep./Oct. 2007, vol. 56, No. 5, 323-331.
Barton et al, "A double-blind, placebo-cotrolled trial of a topical treatment for chemotherapy-induced peripheral neuropathy: NCCTG trial N06CA," Support Care Cancer, Jun. 2011, vol. 19, No. 6, pp. 833-841 (NIH Public Access Author Manuscript—18 pages).
Bhatnagar et al, "Chemotherapy dose reduction due to chemotherapy induced peripheral neuropathy in breast cancer patients receiving chemotherapy in the neoadjuvant or adjuvant settings: a single-center experience," SpringerPlus 2014, 3:366 (6 pages).
Bouillot et al, "Peripheral neuropathy associated with mitochondrial disorders: 8 cases and review of the literature," Journal of the Peripheral Nervous System, 2002, No. 7, pp. 213-220.
Boyette-Davis et al, "Persistent chemoneuropathy in patients receiving the plant alkaloids paclitaxel and vincristine," Cancer Chemother Pharmacol, Mar. 2013, vol. 71, No. 3, pp. 619-626 (NIH Public Access Author Manuscript—15 pages).
Bril, "NIS-LL: The Primary Measurement Scale for Clinical Trial Endpoints in Diabetic Peripheral Neuropathy," European Neurology, 1999; 41 (suppl 1), pp. 8-13.
Cavaletti et al, "Chemotherapy-induced peripheral neurotoxicity," Current Opinion Neurology, Oct. 2015, vol. 28, No. 5, pp. 500-507.
Chaudhry et al, "Toxic neuropathy in patients with preexisting neuropathy," Neurology, 2003; vol. 60, pp. 337-340.
Chaudhry et al, "Characteristics of bortezomib- and thalidomide-induced peripheral neuropathy," Journal of the Peripheral Nervous System, Dec. 2008, vol. 13, No. 4, pp. 275-282 (NIH Public Access Author Manuscript—17 pages).
Cioroiu et al, "Update on Chemotherapy-Induced Peripheral Neuropathy," Curr Neurol Neurosci Rep, 2017, 17:47 (8 pages).
Coppini et al, "The natural history of diabetic peripheral neuropathy determined by a 12 year prospective study using vibration perception thresholds," Journal of Clinical Neuroscience, 2001, vol. 8, No. 6, pp. 520-524.
Facer et al, "Correlation of quantitative tests of nerve and target organ dysfunction with skin immunohistology in leprosy," Brain, 1998, vol. 121, pp. 2239-2247.
Flatters et al, "Ethosuximide reverses paclitaxel- and vincristin-induced painful peripheral neuropathy," Pain, 2004, vol. 109, pp. 150-161.
Galeotti et al, "St. John's Wort reduces neuropathic pain through a hypericin-mediated inhibition of the protein kinase C Y and E activity," Biochemical Pharmacology, 2010, vol. 79, pp. 1327-1336.
Gewandter et al, "A Phase III Randomized, Placebo-Controlled Study of Topical Amitriptyline and Ketamine for Chemotherapy-Induced Peripheral Neuropathy (CIPN): A university of Rochester CCOP study of 462 Cancer Survivors," Support Care Cancer, Jul. 2014, vol. 22, No. 7, pp. 1807-1814 (NIH Public Access Author Manuscript—18 pages).
Gewandter et al, "Painful chemotherapy-induced peripheral neuropathy: lack of treatment efficacy or the wrong clinical trial methodology?," Pain, 2017, vol. 158, No. 1, pp. 30-33 (NIH Public Access Author Manuscript—8 pages).
Gopinath et al, "Increased capsaicin receptor TRPVI in skin nerve fibres and related vanilloid receptors TRPV3 and TRPV4 in keratinocytes in human breast pain," BMC Women's Health, 2005, 5:2 (9 pages).
Grisold et al, "Multifocal neuropathy in vinorelbine treatment for breast cancer (P6.186)," Neurology, Apr. 18, 2017, 88 (16 Supplement) (1 page).
Haim et al, "Full Dose Vincristine (without 2-mg Dose Limit) in the Treatment of Lymphomas," Cancer, May 15, 1994, vol. 73, No. 10, pp. 2515-2519.
Hammack et al, "Phase III evaluation of nortriptyline for alleviation of symptoms of cis-platinum-induced peripheral neuropathy," Pain, 2002, vol. 98, pp. 195-203.
Hansen et al, "Serotonin transporter deficiency protects mice from mechanical allodynia and heat hyperalgesia in vincristine neuropathy," Neuroscience Letters, 2011, vol. 495, pp. 93-97.
Hilkens et al, "Clinical characteristics of severe peripheral neuropathy induced by docetaxel (Taxotere)," Annals of Oncology, 1997, vol. 8, pp. 187-190.
Hirayama et al, "Effect of duloxetine in Japanese patients with chemotherapy-induced peripheral neuropathy: a pilot randomized trial," Int J Clin Oncol, 2015, vol. 20, pp. 866-871.
Jaggi et al, "Mechanisms in cancer-chemotherapeutic drugs-induced peripheral neuropathy," Toxicology, 2012, vol. 291, pp. 1-9.
Jamieson et al, "Nucleolar enlargement, nuclear eccentricity and altered cell body immunostaining characteristics of large-sized sensory neurons following treatment of rats with paclitaxel," NeuroToxicology, 2007, vol. 28, pp. 1092-1098.
Joseph et al, "Oxaliplatin Acts on IB4-Positive Nociceptors to Induce an Oxidative Stress-Dependent Acute Painful Peripheral Neuropathy," The Journal of Pain, vol. 9, No. 5, May 2008, pp. 463-472.

(56) References Cited

OTHER PUBLICATIONS

Joseph et al, "Caspase signalling in neuropathic and inflammatory pain in the rat," European Journal of Neuroscience, vol. 20, 2004, pp. 2896-2902.

Kagiava et al, "The effects of oxaliplatin, an anticancer drug, on potassium channels of the peripheral myelinated nerve fibres of the adult rat," NeuroToxicology, vol. 29, 2008, pp. 1100-1106.

Kandula et al, "Pediatric chemotherapy induced peripheral neuropathy: A systematic review of current knowledge," Cancer Treatment Reviews, vol. 50, 2016, pp. 118-128.

Kautio et al, "Amitriptyline in the Treatment of Chemotherapy-Induced Neuropathic Symptoms," Journal of Pain and Symptom Management, vol. 35, No. 1, Jan. 2008, pp. 31-39.

Kerckhove et al, "Long-Term Effects, Pathophysiological Mechanisms, and Risk Factors of Chemotherapy-Induced Peripheral Neuropathies: A Comprehensive Literature Review," Frontiers in Pharmacology, vol. 8, Article 86, Feb. 2017, pp. 1-17.

Kiya et al, "Role of Satellite Cell-Derived L-Serine in the Dorsal Root Ganglion in Paclitaxel-Induced Painful Peripheral Neuropathy," Neuroscience, 2011, vol. 174, pp. 190-199.

Koskinen et al, "Intraepidermal Nerve Fibre Density in Cancer Patients Receiving Adjuvant Chemotherapy," Anticancer Research, vol. 31, 2011, pp. 4413-4416.

Kroigard et al, "Characterization and diagnostic evaluation of chronic polyneuropathies induced by oxaliplatin and docetaxel comparing skin biopsy to quantitative sensory testing and nerve conduction studies," European Journal of Neurology 2014, vol. 21, pp. 623-629.

Ling et al, "Behavioral and pharmacological description of oxaliplatin-induced painful neuropathy in rat," Pain, 2007, vol. 128, pp. 225-234.

Lynch et al, "A Double-Blind, Placebo-Controlled, Crossover Pilot Trial With Extension Using an Oral Mucosal Cannabinoid Extract for Treatment of Chemotherapy-Induced Neuropathic Pain," Journal of Pain and Symptom Management, Jan. 2014, vol. 47, No. 1, pp. 166-173.

Melzack, "The short-form McGill Pain Questionnaire," Pain, 1987, vol. 30, pp. 191-197.

Mihara et al, "Involvement of spinal NR2B-containing NMDA receptors in oxaliplatin-induced mechanical allodynia in rats," Molecular Pain, 2011, vol. 7, No. 8 (7 pages).

Narayanaswamy et al, "A longitudinal study of sensory biomarkers of progression in patients with diabetic peripheral neuropathy using skin biopsies," Journal of Clinical Neuroscience, 2012, vol. 19, pp. 1490-1496.

Rao et al, "Efficacy of Gabapentin in the Management of Chemotherapy-induced Peripheral Neuropathy," Cancer, Nov. 1, 2007, vol. 110, No. 9, pp. 2110-2118.

Rao et al, "Efficacy of Lamotrigine in the Management of Chemotherapy-induced Peripheral Neuropathy," Cancer, Jun. 15, 2008, vol. 112, No. 12, pp. 2802-2808.

Richardson et al, "Reversibility of symptomatic peripheral neuropathy with bortezomib in the phase III APEX trial in relapsed multiple myeloma: impact of a dose-modification guideline," British Journal of Haematology, 2009, vol. 144, pp. 895-903.

Richardson et al, "Single-Agent Bortezomib in Previously Untreated Multiple Myeloma: Efficacy, Characterization of Peripheral Neuropathy, and Molecular Correlations With Response ad Neuropathy," Journal of Clinical Oncology, Jul. 20, 2009, vol. 27, No. 21, pp. 3518-3525.

Scuteri et al, "Role of MAPKs in platinum-induced neuronal apoptosis," NeuroToxicology, 2009, vol. 30, pp. 312-319.

Seretny et al, "Incidence, prevalence, and predictors of chemotherapy-induced peripheral neuropathy: A systematic review and meta-analysis," Pain, 2014, vol. 155, pp. 2461-2470.

Siau et al, "Dysregulation of Cellular Calcium Homeostasis in Chemotherapy-Evoked Painful Peripheral Neuropathy," Anesth Analg, May 2006, vol. 102, No. 5, pp. 1485-1490 (NIH Public Access Author Manuscript—11 pages).

Siau et al, "Paclitaxel- and vincristine-evoked painful peripheral neuropathies: Loss of epidermal innervation ad activation of Langerhans cells," Exp Neurol, Oct. 2006, vol. 201, No. 2, pp. 507-514 (NIH Public Access Author Manuscript—14 pages).

Siegal et al, "Cisplatin-Induced Peripheral Neuropathy—Frequent Off-Therapy Deterioration, Demyelinating Syndromes, and Muscle Cramps," Cancer, 1990, vol. 66, pp. 1117-1123.

Smith et al, "Effect of duloxetine on pain, function, and quality of life among patients with chemotherapy-induced painful peripheral neuropathy: a randomized clinical trial," JAMA, Apr. 3, 2013, vol. 309, No. 13, pp. 1359-1367 (NIH Public Access Author Manuscript—19 pages).

Sun et al, "Calcium in suramin-induced rat sensory neuron toxicity in vitro," Brain Research, 1996, vol. 742, pp. 149-156.

Ta et al, "Transient Receptor Potential Vanilloid 1 is essential for cisplatin-induced heat hyperalgesia in mice," Molecular Pain, 2010, vol. 6, No. 15 (15 pages).

Tanabe et al, "Paclitaxel-induced peripheral neuropathy in patients receiving adjuvant chemotherapy for breast cancer," Int J Clin Oncol, 2013, vol. 18, pp. 132-138.

Tofthagen, "Patient Perceptions Associated With Chemotherapy-Induced Peripheral Neuropathy," Clinical Journal of Oncology Nursing, Jun. 2010, vol. 14, No. 3, pp. E22-E28.

Van Acker et al, "Automated PGP9.5 immunofluorescence staining: a valuable tool in the assessment of small fiber neuropathy?," BMC Research Notes, 2016, 9:280 (11 pages).

Velasco et al, "Neuropatia inducida por quimioterapia: un problema no resuelto," Neurologia, 2010, vol. 25, No. 2, pp. 116-131 (in Spanish).

Verstappen et al, "Dose-related vincristine-induced peripheral neuropathy with unexpected off-therapy worsening," Neurology, 2005, vol. 64, pp. 1076-1077.

Winters-Stone et al, "Falls, Functioning, and Disability Among Women With Persistent Symptoms of Chemotherapy-Induced Peripheral Neuropathy," Aug. 10, 2017, vol. 35, No. 23, pp. 2604-2614.

Wolf et al, "Chemotherapy-indued peripheral neuropathy: Prevention and treatment strategies," European Journal of Cancer, 2008, vol. 44, pp. 1507-1515.

Yiangou et al, "Molecular forms of NGF in human and rat neuropathic tissues: decreased NGF precursor-like immunoreactivity in human diabetic skin," Journal of the Peripheral Nervous System, 2002, vol. 7, pp. 190-197.

\* cited by examiner

TREATMENT OF PERIPHERAL NEUROPATHY INDUCED BY CANCER CHEMOTHERAPY

FIELD OF THE INVENTION

The present invention concerns the treatment of peripheral neuropathy induced by cancer chemotherapy. More particularly, but not exclusively, this invention concerns a method of treating peripheral neuropathy induced by cancer chemotherapy, comprising administering topically to one or more areas of the skin capsaicin, or a capsaicinoid, or other agonists of TRPV1 (Transient Receptor Potential Cation Channel Subfamily V Member 1), to a patient in need thereof, wherein the capsaicin or capsaicinoid or other TRPV1 agonist is administered after the patient has received cancer chemotherapy, and wherein the patient is not currently receiving cancer chemotherapy. The invention also concerns related methods, including methods of inducing nerve fibre regeneration and products, such as kits for the treatment of peripheral neuropathy induced by cancer chemotherapy.

BACKGROUND OF THE INVENTION

Peripheral neuropathy is a general term used to describe a condition wherein the peripheral nerves (nerves that lie beyond the brain and spinal cord) are damaged. Peripheral neuropathy can be caused, for example, by metabolic disorders, traumatic injuries, immune conditions or infections, or exposure to toxins. Peripheral neuropathy affecting sensory nerves can be painful (for example, it may involve painful shooting sensations, and/or burning pain) or non-painful (for example, it may involve sensations of numbness, loss of balance, or non-painful spontaneous tingling).

Chemotherapy-induced peripheral neuropathy (CIPN) is a specific term used to describe peripheral neuropathy, whether painful or non-painful, which is induced by cancer chemotherapy. CIPN is a common and often disabling adverse effect of many cancer treatments (Wolf et al., *Eur J Cancer.* 2008, 44(11), 1507-1515; Cioroiu et al., *Curr Neurol Neurosci Rep.* 2017, 17(6), 47; Chaudhry et al., *Neurology* 2003, 60(2), 337-340). CIPN may persist for years, and affect the quality of life (Kandula et al., *Cancer Treat Rev.* 2016, 50:118-128; Tofthagen, *Clin J Oncol Nurs.* 2010, 14(3): E22-28; Bakitas, *Nurs Res.* 2007, 56(5): 323-331; Winters-Stone et al., *J Clin Oncol.* 2017, JCO2016713552). CIPN is often cited as a reason for dose-reduction or even discontinuation of chemotherapy treatment, with consequences for prognosis (Richardson et al., *Br J Haematol.* 2009, 144(6): 895-903; Bhatnagar et al., *Springerplus.* 2014, 3:366; Tanabe et al., *Int Clin Oncol.* 2013; 18(1):132-138). Despite the prevalence and impact of CIPN, there is no treatment for its prevention, nor a cure.

More than 30% of patients treated with neurotoxic cancer chemotherapy agents develop CIPN (Seretny et al., *Pain.* 2014, 155(12): 2461-2470). The risk is especially high with cisplatin, paclitaxel, docetaxel, vincristine, oxaliplatin, and bortezomib (Velasco et al., *Neurologia.* 2010, 25(2): 116-131; Cavaletti et al., *Nat Rev Neurol.* 2010; 6(12):657-666). Platinum-based and other drugs may lead to the 'coasting' phenomenon, i.e. an increase in the severity of symptoms of CIPN after cessation of cancer chemotherapy treatment (Siegal et al., *Cancer* 1990, 66(6): 1117-1123; Haim et al., *Cancer* 1994; Grisold et al., *Neurology* 2017; Hilkens et al., *Ann Oncol* 1997, 8(2): 187-190; Verstappen et al., *Neurology.* 2005, 64(6): 1076-1077).

Cancer chemotherapy agents can exert unwanted toxic side-effects on peripheral nerve fibers (Kerckhove et al., *Frontiers in Pharmacology.* 2017, 8:86), causing reduced amplitude of the sensory action potentials, and dysfunction and/or degeneration of small sensory fibers, which may lead to the development of pain (Jaggi et al., *Toxicology.* 2012, 291(1-3):1-9.20). The diverse underlying cellular and molecular mechanisms include loss of intra-epidermal nerve fibers (IENF) (Siau et al., *Anesth Analg.* 2006, 102(5):1485-1490) mitochondrial changes (Bouillot et al., *J Peripher Nerv Syst.* 2002, 7(4):213-220) neuronal viability (Sun et al., *Brain Res.* 1996, 742(1-2):149-156) sodium channels (Ling et al., *Pain.* 2007, 128(3):225-234) potassium channels (Kagiava et al., *Neurotoxicology.* 2008, 29(6):1100-1106) transient receptor potential vanilloid receptors (TRPV) (Ta et al., *Mol Pain.* 2010, 6) Langerhans cells (Siau et al., *Exp Neurol.* 2006, 201(2):507-514) oxidative stress (Joseph et al, *J Pain.* 2008, 9(5):463-472) mitogen activated protein kinase (MAPK) (Scuteri et al., *Neurotoxicology.* 2009, 30(2):312-319) N-methyl-d-aspartate (NMDA) receptors (Flatters et al., *Pain.* 2004, 109(1-2):150-161) neuropeptide Y (Jamieson et al., *Neurotoxicology.* 2007, 28(6):1092-1098) nitric oxide (Mihara et al., *Mol Pain.* 2011, 7:8) 5-HT2A (Hansen et al., *Neurosci Lett.* 2011, 495(2):93-97) protein kinase C (Galeotti et al., *Biochem Pharmacol.* 2010, 79(9):1327-1336) calpains and caspases (Joseph et al., *Eur J Neurosci.* 2004, 20(11):2896-2902) and phosphoglycerate dehydrogenase (3PGDH) (Kiya et al., *Neuroscience.* 2011, 174:190-199). The involvement of small sensory fibers in CIPN has been well documented (Koskinen et al., *Anticancer Res* 2011, 31(12):4413-4416; Krøgdrd et al., *Eur J Neurol* 2014, 21(4):623-629; Boyette-Davis et al., *Cancer Chemother Pharmacol* 2013, 71(3):619-626; Chaudhry et al., *J Peripher Nerv Syst* 2008, 13(4):275-282; Richardson et al., *J Clin Oncol* 2009, 27(21):3518-3525).

Randomized clinical trials have been conducted with pain reducing drugs that are currently used to treat neuropathic pain, in order to probe their effectiveness in treating painful CIPN, such as Gabapentin (Rao et al., *Cancer.* 2007, 110 (9):2110-2118) Lamotrigine (Rao et al., *Cancer.* 2008, 112 (12):2802-2808) Nortriptyline (Hammack et al., *Pain.* 2002, 98(1-2):195-203) Amitriptyline (Kautio et al., *J Pain Symptom Manage.* 2008, 35(1):31-39) and Duloxetine (Smith et al., *JAMA.* 2013, 309(13):1359-1367; Hirayama et al., *Int Clin Oncol* 2015, 20(5):866-871). Two studies have evaluated the effectiveness of topical agents incorporating Amitriptyline, Ketamine, and Baclofen to treat CIPN (Gewandter et al., *Support Care Cancer.* 2014, 22(7):1807-1814; Barton et al., *Support Care Cancer.* 2011, 19(6):833-841). One study was conducted to determine the effect of an oro-mucosal *cannabis*-based spray on CIPN (Lynch et al., *J Pain Symptom Manage.* 2014, 47(1):166-173). The results of these trials have been largely disappointing (Gewandter et al., *Pain.* 2017, 158(1):30-33) and only Duloxetine showed a small statistical effect on pain outcome measures. None of these studies have reported an effect to promote nerve regeneration or restoration. Thus, there is a need for effective treatments for the prevention and cure of both painful and non-painful CIPN.

Capsaicin is an agonist of TRPV1 (Transient Receptor Potential Cation Channel Subfamily V Member 1), a non-selective, cation channel that functions as an integrator of noxious chemical and physical stimuli. Topical capsaicin formulations can be used to manage pain. For example, low-concentration creams are currently available for daily skin application over the course of several weeks. Resiniferatoxin (RTX), a chemical in resin spurge (*Euphorbia*

*resinifera*), a cactus-like plant from Africa), is a potent agonist of TRPV1, and has similar effects to capsaicin from chili peppers (Apostolidis et al., *Urology*, 2005, 65(2):400-5. Abooj et al., *The Open Pain Journal*, 2016, 9, 1-14.)

Capsaicin 8% Patch (also known as the Capsaicin 179 mg Cutaneous Patch, or Qutenza®, and available from Grünenthal Ltd) is considered an effective, safe and well tolerated topical treatment for the relief of neuropathic pain. Application of this high-dose cutaneous patch to an area of skin can reduce neuropathic pain after a single 30 to 60 minute application (see, e.g., Webster et al., *BMC Anesthesiol.* 2011, 11:25; Anand et al., *Br J Anaesth*, 2011, 107(4):490-502).

The present inventors have found that capsaicin, for example high doses of capsaicin, such as Capsaicin 8% Patch, can provide significant relief of pain in CIPN, when administered to a patient after the patient has received cancer chemotherapy, when the patient is not currently receiving cancer chemotherapy (Anand et al., *J Pain Res,* 2019, 12: 2039-2052).

It is thought that capsaicin can alleviate pain in patients suffering from painful CIPN. Capsaicin 8% Patch is at present licensed in the EU for peripheral neuropathic pain. Without wishing to be bound by theory, it is thought that capsaicin alleviates pain by overstimulating skin nociceptors, leading to the skin nociceptors being temporarily incapacitated (i.e., defunctionalized") (Anand et al., *Br J Anaesth*, 2011, 107(4):490-502).

Previous studies of the effect of various topical capsaicin formulations on skin have shown degeneration of cutaneous sensory nerve terminals (as a part of "defunctionalisation") followed by regeneration, e.g. regeneration over 3 months after a single Capsaicin 8% Patch application (see Anand et al., *Br J Anaesth*, 2011, 107(4):490-502; Rage et al., *Clin Neurophysiol*, 2010, 121(8), 1256-1266). However, studies which were concerned with the effect of capsaicin in relation to diabetes, and particularly diabetic neuropathy, reported intra-epidermal nerve fibre regeneration following topical capsaicin that was incomplete and slower than in healthy human volunteers (Kennedy et al., *J Pain.* 2010; 11:579-587, Polydefkis et al., *Brain* 2004; Khoshnoodi et al., *Ann Clin Transl Neurol*, 2019; 6: 2088-2096). There have been no studies of nerve fiber regeneration in CIPN patients following topical capsaicin treatment (other than Anand et al., *J Pain Res*, 2019, 12: 2039-2052), nor any studies on the effect of capsaicin on sub-epidermal nerve fibres, nor any analysis of a range of nerve biomarkers following high dose topical capsaicin (e.g. Capsaicin 8% Patch).

Surprisingly, the present inventors have found that in addition to any pain relief and temporary incapacitation of skin nociceptors, administering high doses of capsaicin (e.g. Capsaicin 8% Patch) to a patient suffering from painful CIPN, after the patient has received cancer chemotherapy, and when the patient is no longer receiving chemotherapy, can also induce significant nerve fiber regeneration and restoration of the previous nerve fibre density and characteristics (i.e. phenotype), and this can be an effect of Capsaicin 8% Patch treatment for CIPN. Without wishing to be bound by theory, it is thought that cancer chemotherapy agents induce abnormalities in cutaneous sensory nerve terminals, as a part of CIPN. The present invention is based on the realisation that capsaicin (particularly high doses of capsaicin) when administered to patients suffering from CIPN, induces marked and deep cutaneous nerve terminal axotomy, i.e. 'pruning' of the abnormal nerve fiber terminals. Such marked and deep nerve terminal axotomy stimulates thorough regeneration of the axotomized abnormal nerve terminals. Moreover, the regenerated nerve terminals can now interact normally with their target skin cells (which were also affected along with nerve fibers during chemotherapy, but which normalise when patients are no longer receiving chemotherapy). Further, the invention is based on the realisation that when capsaicin is administered after cancer chemotherapy is complete (when the patient is no longer receiving cancer chemotherapy), this capsaicin-induced nerve fibre regeneration, and restoration of nerve fibre density and nerve fibre characteristics (phenotype, such as expression of receptors/ion channels), and interactions with cells in the target organ (keratinocytes), can occur without the risk of further abnormalities (Anand et al., J Pain Res 2019, 12: 2039-2052).

SUMMARY OF THE INVENTION

According to a first aspect, the present invention provides a method of treating peripheral neuropathy induced by cancer chemotherapy, comprising administering topically to one or more areas of the skin capsaicin or a capsaicinoid or other TRPV1 agonist to a patient in need thereof, wherein the capsaicin or capsaicinoid or other TRPV1 agonist is administered after the patient has received cancer chemotherapy, and wherein the patient is not currently receiving cancer chemotherapy.

According to a second aspect of the invention, there is also provided a kit comprising a cutaneous patch and a leaflet, wherein the cutaneous patch contains about 500 to about 700 µg of capsaicin or a capsaicinoid per $cm^2$ of patch, and wherein the leaflet provides instructions for a method of treating peripheral neuropathy induced by cancer chemotherapy, comprising administering the cutaneous patch to one or more areas of the skin of a patient in need thereof, wherein the cutaneous patch is administered after the patient has received cancer chemotherapy, and wherein the patient is not currently receiving cancer chemotherapy.

According to a third aspect of the invention, there is also provided a method of stimulating the regeneration of peripheral sensory nerve fibres comprising administering capsaicin or a capsaicinoid or other TRPV1 agonist to a patient in need thereof, wherein the capsaicin or capsaicinoid or TRPV1 agonist is administered after the patient has received cancer chemotherapy, and wherein the patient is not currently receiving cancer chemotherapy.

It will of course be appreciated that features described in relation to one aspect of the present invention may be incorporated into other aspects of the present invention. For example, the methods of the invention may incorporate any of the features described with reference to the kit of the invention and vice versa.

DESCRIPTION OF THE DRAWINGS

Embodiments of the present invention will now be described by way of example only with reference to the accompanying schematic drawings of which.

Shown in (c) is a bar chart of intra-epidermal nerve fibers for PGP 9.5 counts, and shown in (d) is a bar chart of sub-epidermal (SENF) analysis (% area).

Figure 3:
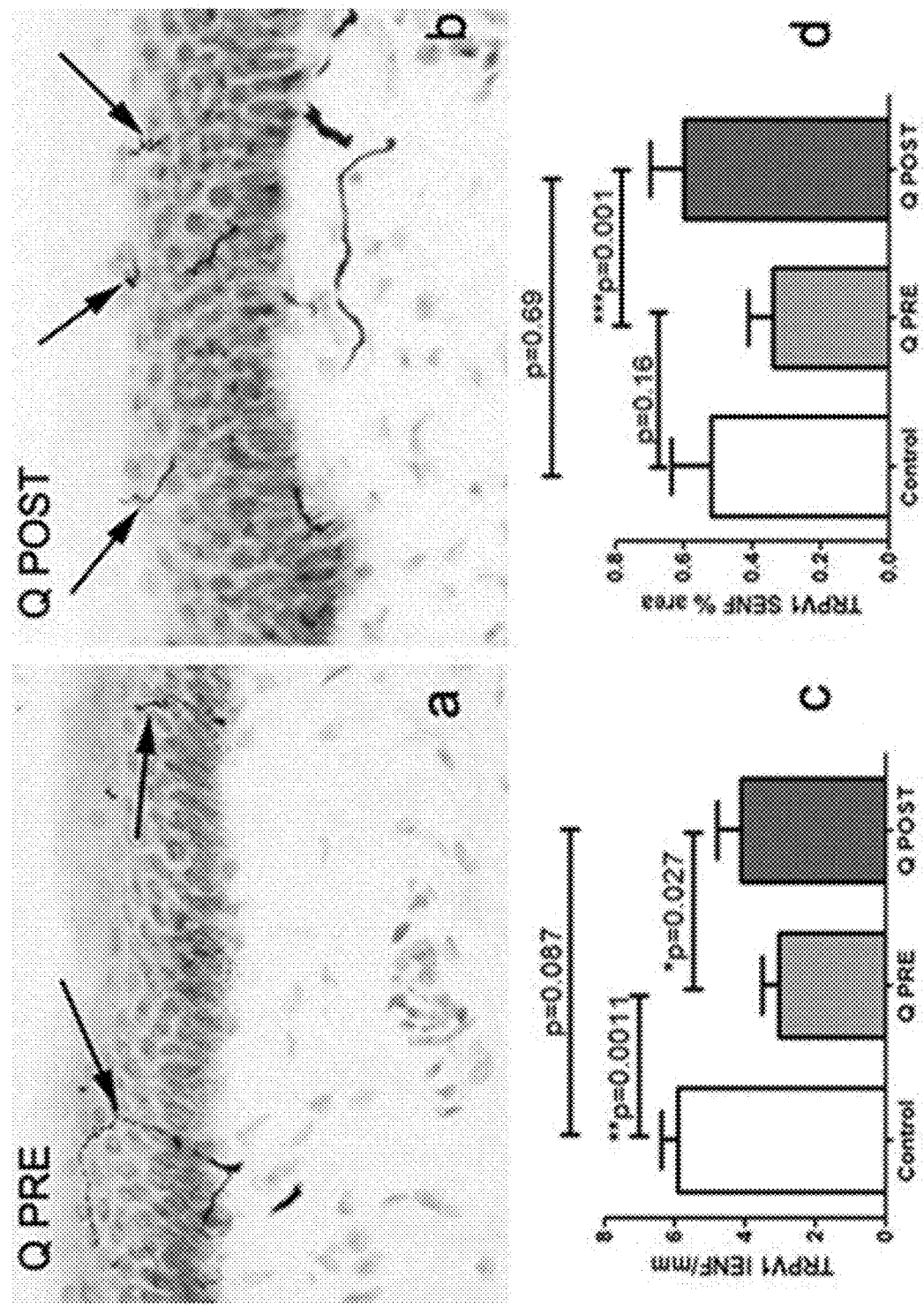

FIG. 3 shows immunohistochemistry in skin biopsies for TRPV1, before and after Capsaicin 8% Patch treatment. Shown in (a) are intra-epidermal nerve fibers (arrowed) and sub-epidermal nerve fibers at the baseline visit (Q PRE), magnification ×40. Shown in (b) are intra-epidermal nerve fibers (arrowed) and sub-epidermal nerve fibers after Capsaicin 8% Patch treatment (Q POST), magnification ×40. Shown in (c) is a bar chart of intra-epidermal nerve fibers for TRPV1 (IENF) counts; shown in (d) is a bar chart of sub-epidermal (SENF) analysis (% area) for TRPV1.

Figure 4:
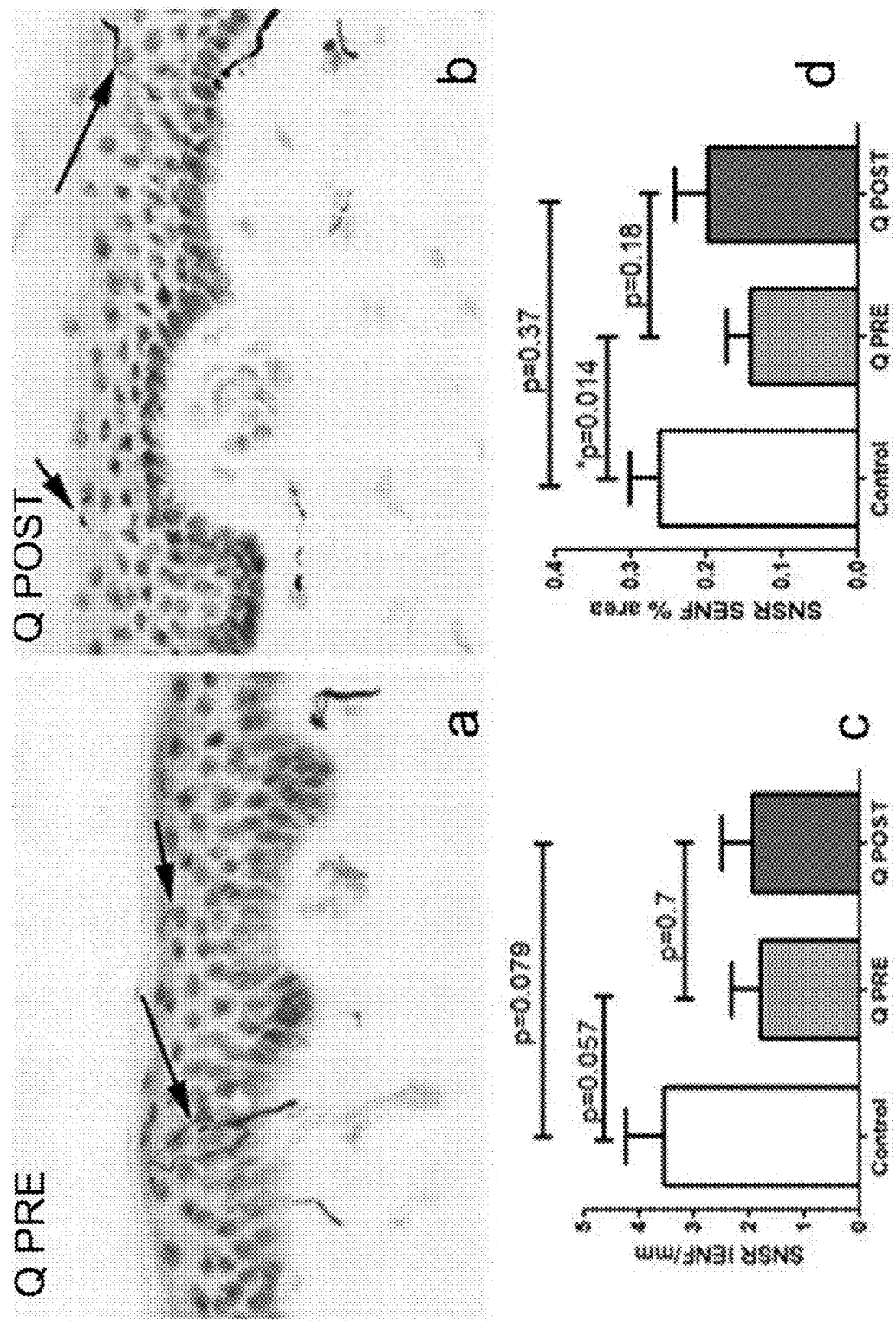

FIG. 4 shows immunohistochemistry in skin biopsies for SNSR, before and after Capsaicin 8% Patch treatment. Shown in (a) are intra-epidermal nerve fibers (arrowed) and sub-epidermal nerve fibers at the baseline visit (Q PRE), magnification ×40. Shown in (b) are intra-epidermal nerve fibers (arrowed) and sub-epidermal nerve fibers after Capsaicin 8% Patch treatment (Q POST), magnification ×40. Shown in (c) is a bar chart of intra-epidermal nerve fibers for SNSR (IENF) counts; shown in (d) is a bar chart of sub-epidermal (SENF) analysis (% area) for SNSR.

Figure 5:
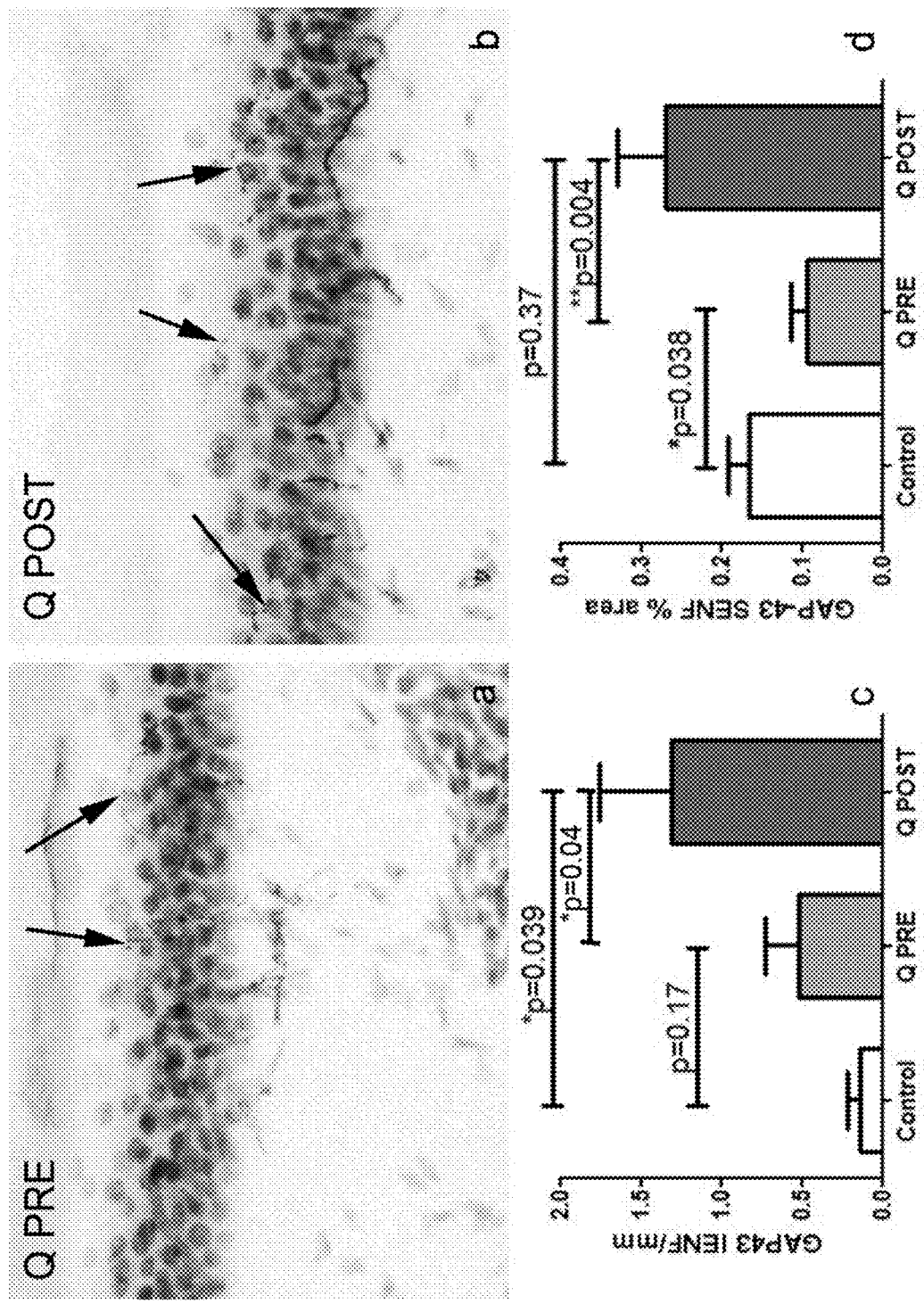

FIG. 5 shows immunohistochemistry in skin biopsies for GAP43, before and after Capsaicin 8% Patch treatment. Shown in (a) is a representative image of intra-epidermal nerve fibers (arrowed) and sub-epidermal nerve fibers at the baseline visit (Q PRE), magnification ×40. Shown in (b) is a representative image of intra-epidermal nerve fibers (arrowed) and sub-epidermal nerve fibers, after Capsaicin 8% Patch treatment (Q POST), magnification ×40. Shown in (c) is a bar chart of intra-epidermal nerve fibers for GAP43 (IENF) counts; shown in (d) is a bar chart of sub-epidermal (SENF) analysis (% area) for GAP43.

Figure 6:
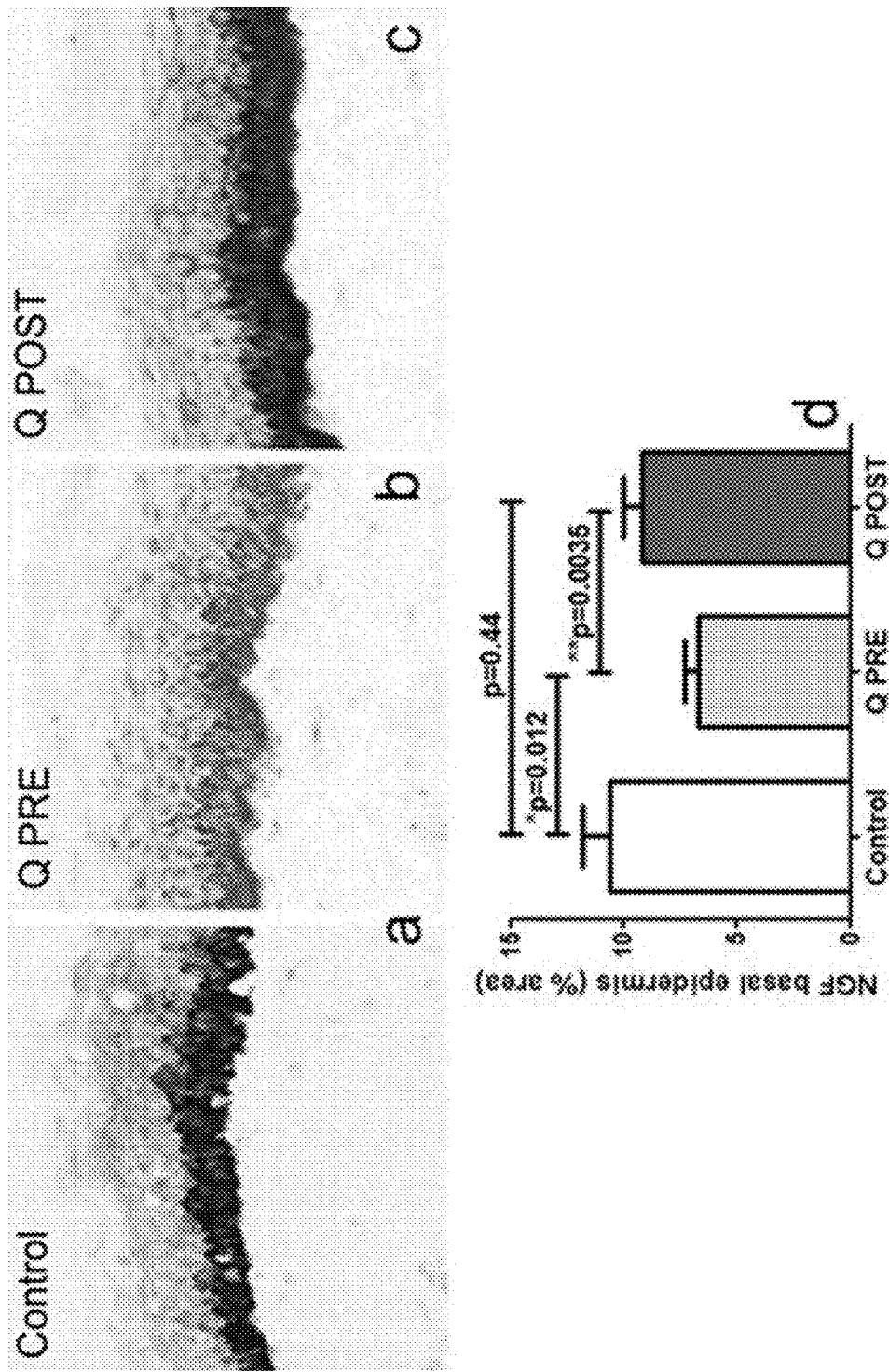

FIG. 6 shows immunohistochemistry in skin biopsies for NGF, before and after Capsaicin 8% Patch treatment. NGF immunostaining of basal epidermis in calf skin obtained from control subjects is shown in (a), control, magnification ×40. NGF immunostaining of basal epidermis in calf skin obtained from CIPN patients before Capsaicin 8% Patch treatment is shown in (b), Q PRE, magnification ×40. NGF immunostaining of basal epidermis in calf skin obtained from CIPN patients after Capsaicin 8% Patch treatment is shown in (c), Q POST, magnification ×40. Shown in (d) is a bar chart of the basal cell NGF image analysis (% area).

Figure 7:
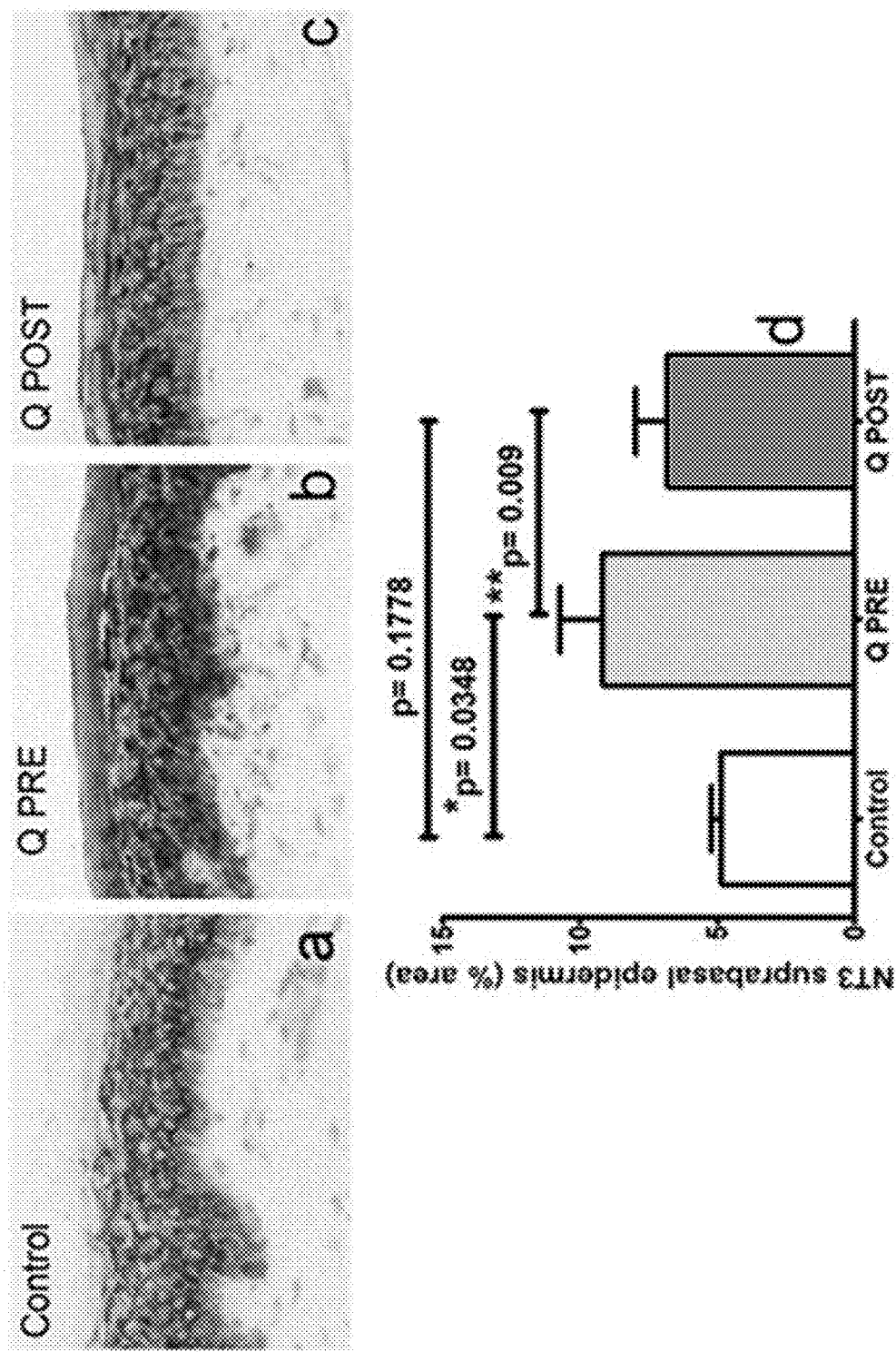

FIG. 7 shows immunohistochemistry in skin biopsies for NT3, before and after Capsaicin 8% Patch treatment. Shown in (a) is NT3 immunostaining from control subjects. Shown in (b) is NT3 immunostaining for CIPN patients before Capsaicin 8% Patch treatment, Q PRE. Shown in (c) is NT3 immunostaining for CIPN patients after Capsaicin 8% Patch treatment, Q POST. Shown in (d) is a bar chart for NT3 suprabasal image analysis (% area).

Figure 8:
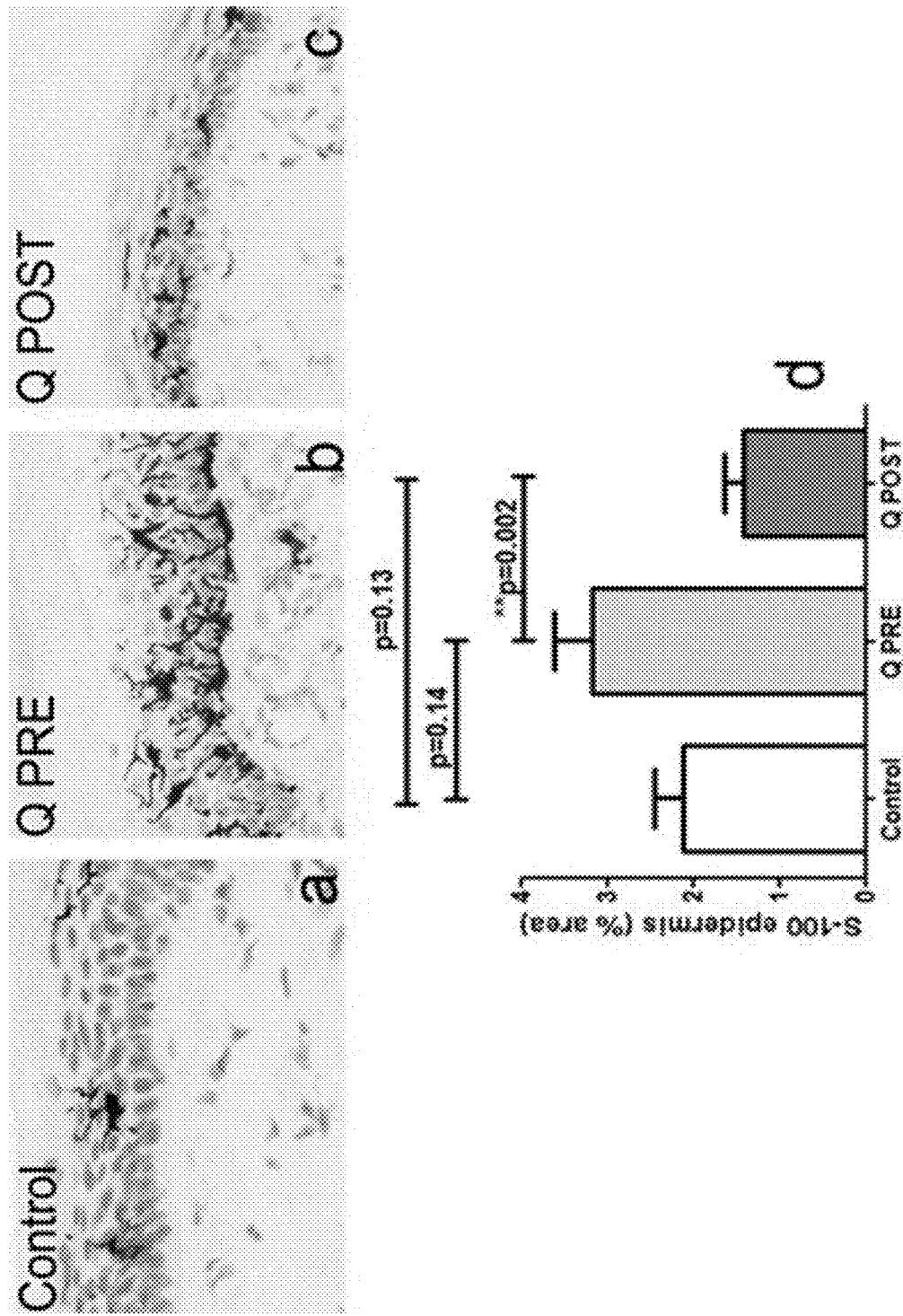

FIG. 8 shows immunohistochemistry in skin biopsies for Langerhans cells (LCs), before and after Capsaicin 8% Patch treatment. Shown in (a) is LCs immunostaining in the epidermis of calf skin from control subjects, magnification ×40. Shown in (b) is LCs immunostaining in the epidermis of calf skin from CIPN patients before Capsaicin 8% Patch treatment, Q PRE, magnification ×40. Shown in (c) is LCs immunostaining in the epidermis of calf skin from CIPN patients after Capsaicin 8% Patch treatment, Q POST, magnification ×40. Shown in (d) is a bar chart of LCs image analysis (% area).

DEFINITIONS

Peripheral Neuropathy

Peripheral neuropathy refers to a condition wherein the peripheral nerves (nerves that lie beyond the brain and spinal cord) are damaged. Exemplary causes of peripheral neuropathy include metabolic disorders, immune conditions or infections, traumatic injuries, and exposure to toxins. Peripheral neuropathy can be chronic (chronic peripheral neuropathy refers to long-lasting peripheral neuropathy, persisting for more than a few months, for example more than 3 months, or more than 6 months).

Peripheral neuropathy affecting sensory nerves can be painful. Painful peripheral neuropathy refers to peripheral neuropathy resulting in painful symptoms, and may involve chronic pain (chronic pain refers to long-lasting pain, persisting for more than a few months, for example more than 3 months, or more than 6 months). For example, patients suffering from painful peripheral neuropathy may experience shooting and/or burning pain, and the like. Painful peripheral neuropathy can involve allodynia. Allodynia refers to pain elicited by a stimulus that, in the case of a healthy subject (as opposed to a subject experiencing allodynia, such as allodynia resulting from peripheral neuropathy) would not normally cause pain. Painful peripheral neuropathy can involve painful dysesthesia. Painful dysesthesia involves a painful, unpleasant and abnormal sensation of touch, for example sensations such as burning of the skin and/or sensations of electric shock. Painful peripheral neuropathy can involve episodic neuropathic pain or continuous neuropathic pain. Episodic neuropathic pain refers to recurring pain, typically involving periods of pain (for example, paroxysmal pain) interspersed with periods of relative comfort wherein the pain is alleviated. Continuous neuropathic pain refers to neuropathic pain that is substantially constant, and typically chronic.

Peripheral neuropathy affecting sensory nerves can be non-painful. Non-painful peripheral neuropathy refers to peripheral neuropathy resulting in non-painful symptoms. For example, patients suffering from non-painful peripheral neuropathy may experience symptoms of reduction in sensation, numbness, loss of balance, spontaneous non-painful tingling and the like.

Painful and non-painful neuropathy are not mutually exclusive, and may be experienced together by a single patient.

Cancer

Cancer refers to a pathological condition typically characterized by unregulated cell growth. Cancer as described herein includes benign and malignant cancers as well as dormant tumors and micrometastases. It includes tumours of epithelial cells (carcinomas), the blood or bone marrow (leukemias, lymphomas), connective tissues (sarcomas) and cancers in other cells types (for example brain cancers, blastomas).

Chemotherapy; Cancer Chemotherapy

As used herein, the term chemotherapy refers to chemotherapy for the treatment of cancer, i.e. cancer chemotherapy. Cancer chemotherapy refers to the therapeutic use of chemical agents to treat cancer. More particularly, cancer chemotherapy typically involves the administration of one or more cytotoxic drugs to destroy or inhibit the growth and division of malignant cancerous cells. As used herein, the term chemotherapy agent, which can be used interchangeably with the term chemotherapeutic agent, refers to a chemical agent used in the treatment of cancer, more particularly a cytotoxic drug used to destroy or inhibit the growth and division of malignant cancerous cells. The term neurotoxic chemotherapy agent, which can be used interchangeably with the term neurotoxic chemotherapeutic agent, refers to a chemotherapeutic agent that exhibits toxicity towards cells of the nervous system. Examples of neurotoxic chemotherapeutic agents include cisplatin, paclitaxel, docetaxel, vincristine, oxaliplatin, and bortezomib.
Chemotherapy-Induced Peripheral Neuropathy (CIPN)

As used herein, the term chemotherapy-induced peripheral neuropathy (CIPN) refers to peripheral neuropathy, whether painful or non-painful, caused by cancer chemotherapy. CIPN can, for example, lead to symptoms such as pain, numbness, tingling and sensitivity to cold in the hands and feet. CIPN often develops shortly after the first dose of chemotherapy is administered to a patient undergoing a course of treatment by chemotherapy. CIPN often increases in severity as treatment continues, with a plateau being observed in its severity once the course of treatment by chemotherapy is complete. However, when platinum-based drugs (for example, cisplatin, oxaliplatin and carboplatin) are used in the cancer chemotherapy, the severity of CIPN may continue to increase for several months after the course of treatment by cancer chemotherapy ends. Whether CIPN develops, and its severity, depends on the chemotherapeutic agent or agents used, the duration of the course of treatment, and the total amount of the one or more agents administered to the patient over the course of treatment by cancer chemotherapy.

Without wishing to be bound by theory, it is thought that cancer chemotherapy agents give rise to CIPN by inducing abnormalities in peripheral nerves, and thereby affecting cutaneous sensory nerve terminals. Cutaneous nerve terminals are nerve terminals of nerve fibers found in the skin, including, for example, sub-epidermal nerve fibers and intra-epidermal nerve fibers—small sensory nerve fibers mediate pain and temperature sensation.
Remission from Cancer As used herein, the term remission from cancer refers to a reduction in or disappearance of the signs and symptoms of cancer, compared to the signs and symptoms typically arising from a progressive cancer. The term partial remission refers to a partial decrease in the severity of the signs and symptoms of cancer, compared to the signs and symptoms typically arising from a progressive cancer. For example, partial remission may occur during and/or after completion of a course of cancer chemotherapy by the patient in question. The term complete remission refers to remission wherein all of the signs and symptoms of cancer have disappeared. Complete remission may occur after completion of a course of cancer chemotherapy by the patient. It will be appreciated that even in complete remission, the cancer may nonetheless still be present in one or more tissues, without giving rise to signs or symptoms.
Capsaicin A molecule of capsaicin (8-methyl-N-vanillyl-6-nonenamide; IUPAC name (6E)-N-[(4-Hydroxy-3-methoxyphenyl) methyl]-8-methylnon-6-enamide) has the following structure:

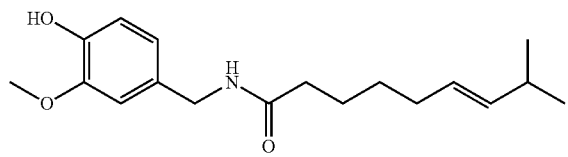 [SMILES: COc1cc(CNC(=O)CCCC/C=C/C(C)C)ccc1O]

Capsaicin is a highly selective agonist for the transient receptor potential vanilloid 1 receptor (TRPV1). Capsaicin is found in some plants belonging to the genus *Capsicum*, which are members of the nightshade family, Solanaceae. Capsaicin is typically found in the fruit of some (but not all) of the plants belonging to the genus *Capsicum* that are commonly known as chili peppers. Capsaicin is typically present in these plants alongside other capsaicin derivatives known as capsaicinoids (e.g. dihydrocapsaicin, nordihydrocapsaicin, homocapsaicin, and homodihydrocapsaicin). For example, *Capsicum chinense* is a species of chili pepper that includes capsaicin-containing varieties, such as habanero, Datil and Scotch bonnet.
Capsaicinoids Capsaicinoids are a group of compounds with similar structure and function as capsaicin. According to the present invention the term may include one or more of the following compounds: dihydrocapsaicin, nordihydrocapsaicin, homocapsaicin, homodihydrocapsaicon and nonivamide. Certain preferred embodiments of the invention relate to capsaicin or dihydrocapsaicin (ie, dihydrocapsaicin is the preferred capsaicinoid). In many embodiments of all aspects of the invention capsaicin is the preferred compound (ie, capsaicin in preferred over an alternative capsaicinoid).
Other TRPV1 Agonists These include Resiniferatoxin (RTX), a chemical in cactus-like plants from Africa (resin spurge, *Euphorbia resinifera, Euphorbia poissonii*) and derivatives thereof. According to certain embodiments of all aspects of the invention a compound is regarded as a TRPV1 agonist if it activates TRPV1. That activation may be measured using any suitable assay for example a patch-clamp assay. Suitable assays are routine as evidenced by the fact that they are available commercially on a contract basis for example from SB Drug Discovery Ltd, Glasgow, UK. According to certain embodiments, TRPV1 agonists show at least 20% or at least 50% or at least 100% or at least 200% of TRPV1 activation as does capsaicin in an identical assay. It is especially preferred if the TRPV1 agonist is fat soluble.

These include Resiniferatoxin (RTX), has the IUPAC name [(1R,6R,13R,15R,17R)-13-Benzyl-6-hydroxy-4,17-dimethyl-5-oxo-15-(prop-1-en-2-yl)-12,14,18-trioxapentacyclo[11.4.1.0.$^{1,10}$.0$^{2,6}$.0$^{11,15}$]octadeca-3,8-dien-8-yl] methyl 2-(4-hydroxy-3-methoxyphenyl)acetate. A molecule of Resiniferatoxin has the following structure:

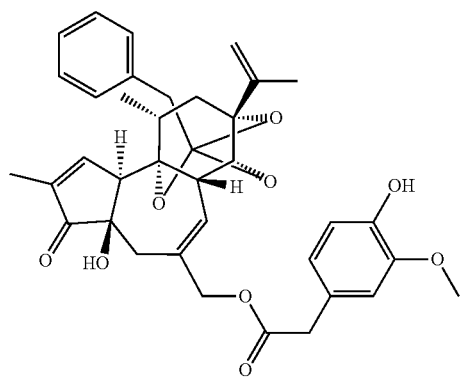

Capsaicin 8% Patch

"Capsaicin 8% Patch" (Capsaicin 179 mg cutaneous patch) is the non-proprietary name for a cutaneous patch comprising capsaicin, which is also sold under the trade name Qutenza®. Capsaicin 8% Patch is obtainable from Grünenthal Ltd, Units 1 and 2 Stokenchurch Business Park, Ibstone Road, Stokenchurch, Buckinghamshire, HP14 3FE, United Kingdom. Capsaicin 8% Patch consists of a 280 cm$^2$ cutaneous patch, which contains a total of 179 mg of capsaicin, that is, 640 μg of capsaicin per cm$^2$ patch. Capsaicin 8% Patch measures 14 cm×20 cm (280 cm$^2$) and consists of an adhesive side and an outer surface backing layer, the capsaicin-containing patch matrix being disposed on the adhesive side. Capsaicin 8% Patch comprises 8% capsaicin by weight, wherein the % by weight of capsaicin is measured relative to the total weight of all of the components in the patch matrix. The adhesive side is covered with a removable, clear, unprinted, diagonally cut, release liner. The outer surface of the backing layer is imprinted with "capsaicin 8%".

The patch matrix typically comprises silicone adhesives, diethylene glycol monoethyl ether, silicone oil, and ethylcellulose N50. The patch backing layer is typically formed from a polyethylene terephthalate (PET) film. The patch removable protective layer (release liner) is typically formed from a fluoropolymer-coated polyester film.

Nerve Fiber Regeneration and/or Restoration

Nerve fiber regeneration refers to the sprouting and elongation of nerve fibers which have been previously damaged or destroyed. Nerve fiber regeneration can lead to the full or partial restoration of the density and phenotype of one or more nerve cells to a normalised, healthy condition, compared to the abnormal, damaged condition of nerve cells observed in patients suffering from CIPN. Nerve fiber regeneration and restoration can potentially lead to the full or partial restoration of the function of one or more nerve cells to a normalised, healthy condition, compared to the abnormal, damaged condition of nerve cells observed in patients suffering from CIPN. According to preferred embodiments of all aspects of the invention, nerve fibre regeneration is understood to be the regeneration of a nerve fibre belonging to an existing nerve cell. That is to say, nerve fibre regeneration does not necessarily require an increase in the number of nerve cells. Rather existing nerve cells, which may have previously lost a region of nerve fibre, may see that region of nerve fibre regrow. Nerve fibre regeneration also includes the restoration of density, phenotype and potentially function of a previously dysfunctional nerve fibre i.e. which generated pain sensations. In certain embodiments nerve fibre regeneration may especially include the restoration of functional nerve fibre terminals.

Nerve fiber regeneration can be measured by immunohistochemical analysis of skin biopsies. A statistically significant increase in the count of intra-epidermal and sub-epidermal nerve fibers, observed in immunohistochemical analysis of skin biopsies, can indicate nerve fiber regeneration. A statistically significant increase (for example an increase of at least 10, 20, 30, or 50%) in the count of sub-epidermal nerve fibers, observed in immunohistochemical analysis of skin biopsies, can indicate nerve fiber regeneration. A statistically significant increase in the count of both intra-epidermal nerve fibers and sub-epidermal nerve fibers, observed in immunohistochemical analysis of skin biopsies, can indicate nerve fiber regeneration.

For example, a statistically significant increase in the count of PGP9.5-immunostained intra-epidermal nerve fibers, observed in immunohistochemical analysis of skin biopsies, can indicate nerve fiber regeneration. Similarly, a statistically significant increase in the count of PGP9.5-immunostained sub-epidermal nerve fibers, observed in immunohistochemical analysis of skin biopsies, can indicate nerve fiber regeneration. A statistically significant increase in the count of both PGP9.5-immunostained intra-epidermal nerve fibers and PGP9.5-immunostained sub-epidermal nerve fibers, observed in immunohistochemical analysis of skin biopsies, can indicate nerve fiber regeneration.

A statistically significant increase in the count of GAP43-immunostained intra-epidermal nerve fibers, observed in immunohistochemical analysis of skin biopsies, can indicate nerve fiber regeneration. A statistically significant increase in the count of GAP43-immunostained sub-epidermal nerve fibers, observed in immunohistochemical analysis of skin biopsies, can indicate nerve fiber regeneration. A statistically significant increase in the count of both GAP43-immunostained intra-epidermal nerve fibers and GAP43-immunostained sub-epidermal nerve fibers, observed in immunohistochemical analysis of skin biopsies, can indicate nerve fiber regeneration.

A statistically significant decrease in the count of Langerhans cells can indicate the consequence of nerve fiber regeneration. For example, a statistically significant decrease in the count of S100 antibody-immunostained Langerhans cells, observed in immunohistochemical analysis of skin biopsies, can indicate the consequence of nerve fiber regeneration.

A statistically significant increase in the level of neuronal growth factor (NGF), observed in immunohistochemical analysis of skin biopsies, can indicate the consequence of nerve fiber regeneration.

A statistically significant decrease in the level of neurotrophin-3 (NT-3), observed in immunohistochemical analysis of skin biopsies, can indicate the consequence of nerve fiber regeneration.

It will be appreciated that an increase or decrease in a count or level described herein is measured relative to the level or count observed in immunohistochemical analysis of skin biopsies in a subject having nerve fibers which have are damaged or destroyed, such as a subject who has received cancer chemotherapy.

It will be appreciated that a statistically significant change in a count or level described herein can refer to the count or level approaching or reaching the count or level observed in a control subject who has never before received and is not currently receiving cancer chemotherapy.

The present inventors have found that administering capsaicin to a patient suffering from painful and/or non-painful CIPN, after the patient has received cancer chemotherapy, when the patient is no longer receiving cancer chemotherapy, can induce nerve fiber regeneration.

Without wishing to be bound by theory, it is thought that cancer chemotherapy agents induce abnormalities in cutaneous sensory nerve terminals, leading to CIPN. Cutaneous nerve terminals are nerve terminals found in the skin, including, for example, nerve terminals that are sub-epidermal, or intra-epidermal.

Capsaicin, particularly in high doses, when administered to patients suffering from CIPN, induces cutaneous marked and deep nerve terminal axotomy, i.e. 'pruning' of the abnormal nerve terminals. This, in turn, stimulates thorough nerve fiber regeneration.

When capsaicin is administered after cancer chemotherapy is complete (i.e., the patient is no longer receiving cancer chemotherapy) capsaicin-induced regeneration of nerve cells can occur without the risk of further abnormalities being induced by chemotherapy agents to: i) nerve fibers in the skin, and ii) the skin cells themselves. This can enhance and restore interactions of the nerve fibers with their target organ, which is essential for their normal functions.

Thus, capsaicin administered after cancer chemotherapy has been received, and when cancer chemotherapy is no longer being received, can be effective, not only in treating pain in patients suffering from painful CIPN, but also in nerve fiber regeneration, meaning that capsaicin can be used to treat patients suffering from painful and/or non-painful CIPN.

DETAILED DESCRIPTION

In a first aspect, the present invention provides a method of treating peripheral neuropathy induced by cancer chemotherapy, comprising administering topically to one or more areas of the skin capsaicin or a capsaicinoid or a TRPV1 agonist to a patient in need thereof, wherein the capsaicin or capsaicinoid or a TRPV1 agonist is administered after the patient has received cancer chemotherapy, and wherein the patient is not currently receiving cancer chemotherapy.

In a second aspect, the present invention provides a kit comprising a cutaneous patch and a leaflet, wherein the cutaneous patch contains about 500 to about 700 µg of capsaicin or a capsaicinoid per $cm^2$ of patch, and wherein the leaflet provides instructions for a method of treating peripheral neuropathy induced by cancer chemotherapy, comprising administering the cutaneous patch to one or more areas of the skin of a patient in need thereof, wherein the cutaneous patch is administered after the patient has received cancer chemotherapy, and wherein the patient is not currently receiving cancer chemotherapy.

In a third aspect of the invention, there is also provided a method of stimulating the regeneration of peripheral sensory nerve fibres comprising administering capsaicin or a capsaicinoid or a TRPV1 agonist to a patient in need thereof, wherein the capsaicin or capsaicinoid is administered after the patient has received cancer chemotherapy, and wherein the patient is not currently receiving cancer chemotherapy.

In certain embodiments, methods of the first or third aspect of the invention may include use of a kit as according to the second aspect of the invention.

Peripheral Neuropathy

Peripheral neuropathy refers to a condition wherein the peripheral nerves (nerves that lie beyond the brain and spinal cord) are damaged. In general, peripheral neuropathy can involve damage to one or more sensory, autonomic, and motor nerves. In certain preferred embodiments all aspects of the present event especially concern peripheral neuropathy of sensory nerves, especially, sensory nerves of the skin (i.e. sensory neurons which terminate between or adjacent to skin cells, that is to say nerve cells having cutaneous sensory nerve terminals).

Peripheral neuropathy induced by cancer chemotherapy typically involves damage to the sensory nerves. Without wishing to be bound by theory, it is thought that cancer chemotherapy agents give rise to peripheral neuropathy by inducing abnormalities in cutaneous sensory nerve terminals.

In some embodiments of the methods and kit of the present invention, peripheral neuropathy induced by cancer chemotherapy includes painful peripheral neuropathy. In some embodiments, peripheral neuropathy induced by cancer chemotherapy includes non-painful peripheral neuropathy. In some embodiments, peripheral neuropathy induced by cancer chemotherapy includes both painful peripheral neuropathy and non-painful peripheral neuropathy.

Examples of symptoms and signs of peripheral neuropathy induced by cancer chemotherapy according to the invention include, but are not limited to: painful shooting sensations; burning pain; sensations of numbness; loss of balance; non-painful spontaneous tingling; loss of co-ordination; sharp, stabbing pain; sensations of weakness of the arms and legs; and sensations of receiving an electric shock. In certain embodiments, the symptoms of peripheral neuropathy can include one or more of painful shooting sensations, burning pain, sensations of numbness, loss of balance, and non-painful spontaneous tingling. According to certain embodiments, the peripheral neuropathy in relation to any aspect of the present invention is chronic peripheral neuropathy (i.e., peripheral neuropathy which was exhibited clinical symptoms for at least 1, 3 or 6 months, for example for at least 1, 3 or 6 months after the cessation of chemotherapy treatment).

Capsaicin or Capsaicinoid or TRPV1 Agonist Effective Amount

According to all aspects of the invention the capsaicin or capsaicinoid or TRPV1 agonist is provided in a therapeutically effective amount. The amount of capsaicin or capsaicinoid or TRPV1 agonist which is required to achieve a therapeutic effect will vary with the subject under treatment, including the age, weight, sex, and medical condition of the subject, as well as the severity of the peripheral neuropathy induced by cancer chemotherapy, and the time interval that has elapsed since the subject stopped receiving cancer chemotherapy.

It will be appreciated that capsaicin or a capsaicinoid or a TRPV1 agonist may achieve a therapeutic effect in the methods and/or kit of the present invention.

Administering Capsaicin or a Capsaicinoid

In some embodiments of the methods and kit of the present invention, administering capsaicin or a capsaicinoid or TRPV1 agonist comprises administering capsaicin or a capsaicinoid or TRPV1 agonist topically. Administering capsaicin or a capsaicinoid or TRPV1 agonist topically involves administering capsaicin or a capsaicinoid or TRPV1 agonist to one or more areas of the skin of the patient.

Examples of topical formulations that can be used for the administration of capsaicin or a capsaicinoid include, but are not limited to: creams, foams, gels, lotions, ointments, pastes, powders, tinctures, and cutaneous patches. It should be understood that the topical formulations for use in the administration of capsaicin or a capsaicinoid or TRPV1 agonist may include excipients conventional in the art.

Administering capsaicin topically to one or more areas of skin can comprise administering from about 500 to about 700 µg of capsaicin per $cm^2$ of skin; from about 550 to about 700 µg of capsaicin per $cm^2$ of skin; from about 600 to about 700 µg of capsaicin per $cm^2$ of skin; or from about 620 to about 660 µg of capsaicin per $cm^2$ of skin. For example, administering capsaicin topically to one or more areas of skin can comprise administering about 640 µg of capsaicin per $cm^2$ of skin. Similar dosages of another capsaicinoid or another TRPV1 agonist can be administered topically to one or more areas of skin. Alternatively, the dosage of other capsaicinoids or TRPV1 agonists can be adjusted to take into account differential therapeutic activity levels per molecule relative to capsaicin. For dihydrocapsaicin, the dosage may not need to be adjusted, and the dosages stated above in relation to capsaicin may apply. For the other capsaicinoids the dosage may optionally be increased by about 80% relative to the dosages stated above for capsaicin.

The one or more areas of skin to which capsaicin or a capsaicinoid or TRPV1 agonist is administered can have a total surface area of from about 100 to about 1000 $cm^2$; from about 100 to about 800 $cm^2$; from about 100 to about 600 $cm^2$; from about 100 to about 500 $cm^2$; or from about 100 to about 400 $cm^2$. It will be appreciated that the one or more areas of skin to which capsaicin or a capsaicinoid or TRPV1 agonist is administered can differ from patient to patient, depending on their symptoms and signs of peripheral neuropathy and the extent of the peripheral neuropathy across the body surface. The one or more areas of skin to which capsaicin or a capsaicinoid or TRPV1 agonist is administered can be one or more areas of skin that exhibit symptoms and/or signs of peripheral neuropathy induced by chemotherapy. An ordinarily skilled physician can readily determine the one or more areas of skin for exposure to capsaicin or a capsaicinoid or TRPV1 agonist, for example by touching different areas of skin (or instructing the patient to do that to themselves) and asking the patient whether each area of the skin has symptoms. It may be a useful tool for the planning of the treatment, for record keeping, and for monitoring the treatment for this information to be illustrated on a diagram of the body. Additionally or alternatively, this information may be traced directly onto skin of the patient, using for example an ink pen to mark the skin. Alternatively or additionally, more sensitive or more accurate or more objective information as to the extent of the peripheral neuropathy may be obtained by using neurophysiological testing, whereby a sensory perception threshold or nerve conduction device is used to assess nerve fibre function.

In some embodiments, administering capsaicin or a capsaicinoid or TRPV1 agonist topically comprises administering capsaicin or a capsaicinoid formulated in a cutaneous patch to one or more areas of the skin of the patient. A cutaneous patch can comprise an adhesive side and an outer surface backing layer, and can have a capsaicin-containing or a capsaicinoid-containing or a or TRPV1 agonist-containing patch matrix disposed on the adhesive side. The adhesive side can be covered with a removable release liner.

A cutaneous patch for administering capsaicin or a capsaicinoid or TRPV1 agonist can have a surface area of from about 100 to about 500 cm$^2$; from about 200 to about 400 cm$^2$; from about 250 to about 350 cm$^2$; from about 250 to about 300 cm$^2$; or from about 270 to about 290 cm$^2$. For example, a cutaneous patch for administering capsaicin or a capsaicinoid or TRPV1 agonist can have a surface area of about 280 cm$^2$. It will be appreciated that a patch may be cut to size, to suit the requirements of an individual patient. It should also be understood that two, three, four, five, six or more patches can be applied simultaneously to the skin of the patient, to suit the requirements of an individual patient. An ordinarily skilled physician can readily determine and prescribe an effective patch size required for exposure of one or more areas of the skin to capsaicin or a capsaicinoid. The physician may also find it useful to trim a relatively large patch in order to apply it to a relatively small area of skin. As such, patches of the invention are preferably arranged to be easily cut with scissors.

Capsaicin and capsaicinoids and also certain preferred TRPV1 agonists are highly lipid soluble and minimally water soluble. In consequence, when applied to unbroken skin, very little of the compound enters the circulation. Thus, therapeutic effects are largely localised. It is likely that a certain amount of the compound will dissolve in subcutaneous fat, and that this will provide something of a depot effect, such that the target nerve fibres will continue to be exposed to the compound even after the patch has been removed.

The matrix of a cutaneous patch for administering capsaicin can comprise from about 5 to about 20% by weight capsaicin; from about 5 to about 15% by weight capsaicin; from about 5 to about 10% by weight capsaicin; or from about 6 to about 10% by weight capsaicin. For example, the matrix of a cutaneous patch for administering capsaicin can comprise about 8% by weight capsaicin. It will be appreciated that the % by weight of capsaicin is measured relative to the total weight of the patch matrix, and that capsaicin is typically evenly distributed throughout the patch matrix. The matrix of a cutaneous patch for administering capsaicin can comprise about 500 to about 700 μg of capsaicin per cm$^2$ of patch; from about 550 to about 700 μg of capsaicin per cm$^2$ of patch; from about 600 to about 700 μg of capsaicin per cm$^2$ of patch; or from about 620 to about 660 μg of capsaicin per cm$^2$ of patch. For example, the matrix of a cutaneous patch for administering capsaicin can comprise about 640 μg of capsaicin per cm$^2$ of patch.

Similar dosages of another capsaicinoid or another TRPV1 agonist can be administered topically to one or more areas of skin. Alternatively, the dosage of other capsaicinoids or TRPV1 agonists can be adjusted to take into account differential therapeutic activity levels per molecule relative to capsaicin. For dihydrocapsaicin, the dosage may not need to be adjusted and the dosages stated above in relation to capsaicin may apply. For the other capsaicinoids, the dosage may optionally be increased by about 80% relative to the dosages stated above for capsaicin.

The patch matrix can comprise excipients. Examples of suitable excipients for use in a patch matrix include, but are not limited to: silicone adhesives, diethylene glycol monoethyl ether, silicone oil, and ethylcellulose N50. It should be understood that the patch matrix may include further excipients conventional in the art. The patch backing layer can be formed from a polyethylene terephthalate (PET) film. The patch removable release liner can be formed from a fluoropolymer-coated polyester film.

For reasons of safety, capsaicin and capsaicinoids and TRPV1 agonists should not normally be administered to the skin of, or near, the eyes. Likewise, capsaicin and capsaicinoids and TRPV1 agonists should not normally be administered to mucous membranes. Capsaicin and capsaicinoids and TRPV1 agonists should not normally be administered to the skin of the head, and in particular capsaicin and capsaicinoids and TRPV1 agonists should not normally be administered to the skin of the face. Capsaicin and capsaicinoids and TRPV1 agonists should not normally be administered to broken, irritated or otherwise sensitive areas of skin, for example the skin of the anogenital regions of the body.

The one or more areas of skin to which capsaicin or a capsaicinoid or TRPV1 agonist is administered can be pre-treated with a topical anaesthetic. Alternatively or additionally, the one or more areas of skin to which capsaicin or a capsaicinoid or TRPV1 agonist may be simultaneously treated with a topical anaesthetic. Accordingly, the invention in all its aspects provides and relates to methods of use of compositions containing as their active ingredient a topical anaesthetic and capsaicin or a capsaicinoid or TRPV1 agonist. Additionally or alternatively, the patient may be administered an oral analgesic immediately prior to topical administration of capsaicin or a capsaicinoid or TRPV1 agonist. For example, the patient may receive topical pre-treatment with lidocaine, prilocaine or both lidocaine and prilocaine. Normally any topical anaesthetics can then be removed prior to topical administration of capsaicin or a capsaicinoid or TRPV1 agonist, and the one or more areas of skin can be washed and dried thoroughly, although it may in certain embodiments be desirable to administer the capsaicin or capsaicinoid or TRPV1 agonist simultaneously (in such cases, suitable compositions may be formulated and provided). Additionally or alternatively, a cold pack can be administered before, during or after topical administration of capsaicin or capsaicinoid or TRPV1 agonist. Hairs in the one or more areas of skin can be clipped or otherwise removed before administering capsaicin or a capsaicinoid or TRPV1 agonist topically, but should normally not be shaved (in order to avoid breaking the skin). The treatment area(s) can then be gently washed with soap and water, then dried, before administering capsaicin or a capsaicinoid or TRPV1 agonist topically.

Capsaicin or a capsaicinoid or TRPV1 agonist can be administered topically to one or more areas of skin, then allowed to remain in place for a period of time. In some embodiments, administering capsaicin or a capsaicinoid or TRPV1 agonist topically comprises administering capsaicin or a capsaicinoid or TRPV1 agonist to one or more areas of skin for a period of about 1 to about 90 minutes; about 10 to about 90 minutes; about 20 to about 90 minutes; about 30 to about 90 minutes; about 10 to about 80 minutes; about 20 to about 80 minutes; about 30 to about 80 minutes; about 10 to about 70 minutes; about 20 to about 70 minutes; about 30 to about 70 minutes; about 10 to about 60 minutes; about 20 to about 60 minutes; about 30 to about 60 minutes; about 10 to about 50 minutes; about 20 to about 50 minutes; or about 30 to about 50 minutes. For example, administering capsaicin or a capsaicinoid or TRPV1 agonist topically can comprise administering capsaicin or a capsaicinoid or TRPV1 agonist to one or more areas of skin for a period of about 30 to about 60 minutes. An ordinarily skilled physician can readily determine and prescribe an effective length of time required for exposure of one or more areas of the skin to capsaicin or a capsaicinoid or TRPV1 agonist. As a point of general guidance, skin with a higher level of subcutaneous fat, in particular skin of the plantar surface of the foot, may need a shorter application of capsaicin or a capsaicinoid due to the fat soluble nature of capsaicin and capsaicinoids and of many TRPV1 agonists. As a starting point, approximately 60 minutes may be a suitable period of time for most areas of the skin, and approximately 30 minutes may be a suitable period of time for the plantar surface of the feet.

In some embodiments, capsaicin or a capsaicinoid can be administered topically to more than one area of the skin simultaneously. In some embodiments, capsaicin or a capsaicinoid or TRPV1 agonist can be administered topically to different areas of the skin sequentially. An appropriate time interval between sequential topical administrations of capsaicin or a capsaicinoid or TRPV1 agonist to different areas of the skin can be about 4 weeks, about 5 weeks, about 6 weeks, about 7 weeks, about 8 weeks, about 9 weeks, about 10 weeks, about 11 weeks, about 12 weeks, or more. In some embodiments, capsaicin or a capsaicinoid or TRPV1 agonist can be administered topically to the same area of the skin sequentially. An appropriate time interval between sequential topical administrations of capsaicin or a capsaicinoid or TRPV1 agonist to the same area of the skin can be about 4 weeks, about 5 weeks, about 6 weeks, about 7 weeks, about 8 weeks, about 9 weeks, about 10 weeks, about 11 weeks, about 12 weeks, or more. An ordinarily skilled physician can readily determine and prescribe an effective time interval between sequential topical applications of capsaicin or a capsaicinoid or TRPV1 agonist to the same, or different, areas of the skin.

After removal of topically administered capsaicin or a capsaicinoid or TRPV1 agonist, cleansing gel can be applied to the one or more areas of the skin. The cleansing gel can be left in place for about 30 to about 120 seconds; for about 60 to about 120 seconds; or for about 60 to about 90 seconds. The cleansing gel can then be removed. Removal of the cleansing gel can comprise wiping the cleansing gel from the skin surface, using dry gauze, in order to remove any remaining capsaicin or capsaicinoid from the skin. After the cleansing gel has been wiped off, the one or more areas of skin can be gently washed with soap and water. Optionally, a kit according to the second aspect of the invention may additionally comprise one or more items selected from cleaning gel, gauze, soap and personal protective equipment such as gloves.

An appropriate cleansing gel, for use in cleansing one or more areas of skin to which capsaicin or a capsaicinoid or TRPV1 agonist has been applied, is a cleansing gel comprising about 0.05 to about 0.5 mg/g butylhydroxyanisole; about 0.05 to about 0.45 mg/g butylhydroxyanisole; about 0.05 to about 0.4 mg/g butylhydroxyanisole; or about 0.1 to about 0.3 mg/g butylhydroxyanisole. For example an appropriate cleansing gel can comprise about 0.2 mg/g butylhydroxyanisole. Optionally, the cleansing gel can also contain excipients, including but not limited to: macrogol 300, carbomer, purified water, sodium hydroxide and disodium edetate.

In some embodiments, administering capsaicin or a capsaicinoid or TRPV1 agonist topically comprises administering Capsaicin 8% Patch (ie, Qutenza® or a generic equivalent thereof) to the skin of the patient. Administering Capsaicin 8% Patch can comprise applying Capsaicin 8% Patch to an area of skin, and allowing it to remain in place for a period of time. Where the area of skin is an area of the skin of the feet, Capsaicin 8% Patch can be allowed to remain in place for a period of time of about 20 to about 40 minutes, such as about 25 to about 35 minutes (e.g., about 30 minutes). Where the area of the skin is not an area of skin of the feet, it is typically allowed to remain in place for about 50 to about 70 minutes, such as about 55 to about 65 minutes (e.g. about 60 minutes). In some embodiments wherein Capsaicin 8% Patch is administered to the skin of the patient, Capsaicin 8% Patch can be administered to an area of the skin of the patient, for a period of about 30 minutes to about 60 minutes.

The area of skin to which Capsaicin 8% Patch is administered can be pre-treated with a topical anaesthetic. Additionally or alternatively, the patient may be administered an oral analgesic immediately prior to topical administration of Capsaicin 8% Patch. For example, the patient may receive pre-treatment with lidocaine, prilocaine or both lidocaine and prilocaine. Any topical anaesthetics can then be removed prior to administration of Capsaicin 8% Patch, and the area of the skin can be washed and dried thoroughly. Additionally or alternatively, a cold pack can be administered before, during or after topical administration of Capsaicin 8% Patch. Hairs in the area of the skin can be clipped or otherwise removed before administering Capsaicin 8% Patch. The treatment area(s) can then be gently washed with soap and water, then dried, before administering Capsaicin 8% Patch. Additionally or alternatively, a cold pack can be administered before, during or after patch application, to reduce any pain induced by Capsaicin 8% Patch.

Capsaicin 8% Patch should not be used on or near the eyes or mucous membranes. Capsaicin 8% Patch should not be applied to the skin of the head. In particular, Capsaicin 8% Patch should not be applied to the skin of the face. Capsaicin 8% Patch should not be applied to broken, irritated or otherwise sensitive areas of skin such as the anogenital area of the body.

Hairs in the area of the skin can be clipped, or otherwise removed, before applying Capsaicin 8% Patch, in order to promote patch adherence (although the skin should not be shaved, in order to avoid breaking the skin). If hairs are removed in this way, the treatment area(s) can then be gently washed with soap and water, then thoroughly dried.

It will be appreciated that Capsaicin 8% Patch is a single use patch. Capsaicin 8% Patch can be cut to match the size and shape of the area of skin. If the patch is to be cut in this manner, it should be cut prior to removal of the release liner. The release liner should not be removed until just prior to application. To apply the patch, a section of the release liner can be peeled away and folded, exposing the adhesive side of the patch. The adhesive side of the patch can then be placed on the area of skin. The patch can then be held in place. The release liner can slowly and carefully be peeled from underneath, while the patch is simultaneously smoothed onto the skin, to ensure that there is contact between the patch and the skin. To ensure the patch remains in contact with the area of the skin during use, stretchable socks or rolled gauze can be applied over the patch to hold it in place.

Typically, Capsaicin 8% Patch is removed gently and slowly by rolling it inward, without the patch being allowed to come into contact with any other area of the skin.

After removal of Capsaicin 8% Patch, cleansing gel is typically applied to the area of the skin to which Capsaicin 8% Patch has been applied. The cleansing gel can be left in place for about 30 to about 120 seconds, such as for about 60 to about 120 seconds (e.g. for about 60 to about 90 seconds). The cleansing gel can then be removed. Removal of the cleansing gel typically comprises wiping the cleansing gel off the skin surface, using dry gauze, in order to remove any remaining capsaicin from the skin. After the cleansing gel has been wiped off, the area can be gently washed with soap and water.

An appropriate cleansing gel, for use in cleansing an area of the skin to which capsaicin has been applied, is a cleansing gel comprising about 0.05 to about 0.5 mg/g butylhydroxyanisole; about 0.05 to about 0.45 mg/g butylhydroxyanisole; about 0.05 to about 0.4 mg/g butylhydroxyanisole; or about 0.1 to about 0.3 mg/g butylhydroxyanisole. For example an appropriate cleansing gel can comprise about 0.2 mg/g butylhydroxyanisole. Optionally, the cleansing gel can also contain excipients, including but not limited to: macrogol 300, carbomer, purified water, sodium hydroxide and disodium edetate. It should be understood that the cleansing gel may include further excipients conventional in the art.

Optionally, a kit according to the second aspect of the invention comprising Capsaicin 8% Patch may additionally comprise one or more items selected from cleaning gel, gauze, soap and personal protective equipment such as gloves.

Nerve Fiber Regeneration

Without wishing to be bound by theory, it is thought that cancer chemotherapy agents give rise to chemotherapy-induced peripheral neuropathy (CIPN) by inducing abnormalities in cutaneous sensory nerve terminals. Cutaneous nerve terminals are nerve terminals of nerve fibers found in the skin, including, for example, sub-epidermal nerve fibers and intra-epidermal nerve fibers.

It has been discovered that capsaicin, when administered to patients suffering from CIPN, induces marked and deep cutaneous nerve terminal axotomy, i.e. comprehensive pruning of the abnormal nerve fiber terminals. This in turn stimulates the thorough regeneration of the axotomized abnormal nerve terminals. Moreover, these regenerated nerve terminals can interact normally with their target skin cells (which are also affected along with nerve fibres during chemotherapy, but which normalise when patients are no longer receiving chemotherapy). When capsaicin or a capsaicinoid is administered after a patient has stopped receiving cancer chemotherapy, capsaicin-induced or capsaicinoid-induced regeneration of nerve fibres can occur without the risk of further abnormalities.

In short, administering capsaicin or a capsaicinoid can induce regeneration of peripheral nerve fibers in patients suffering from painful and/or non-painful peripheral neuropathy induced by cancer chemotherapy. Regeneration of peripheral nerve fibers can comprise capsaicin-induced or capsaicinoid-induced nerve terminal axotomy, followed by regeneration of the axotomized nerve terminals.

Accordingly, in a third aspect, the present invention provides a method of stimulating the regeneration of peripheral sensory nerve fibres comprising administering capsaicin or a capsaicinoid or TRPV1 agonist to a patient in need thereof, wherein the capsaicin or capsaicinoid or TRPV1 agonist is administered after the patient has received cancer chemotherapy, and wherein the patient is not currently receiving cancer chemotherapy. Embodiments of this aspect of the invention include those wherein the capsaicin or capsaicinoid or TRPV1 agonist is as described herein optionally in combination with a patient, chemotherapy and method of administration (for example by patch) as described herein.

Clinical Benefits

Patients treated in accordance with the methods of the first or third aspects of the present invention or by use of a kit according to the second aspect of the invention can report significant pain reduction following treatment with capsaicin or a capsaicinoid or TRPV1 agonist, as measured by the Numerical Pain Rating Scale (NPRS). For example, patients treated in accordance with the present invention can report a reduction in spontaneous pain, as measured by the NPRS, of from about 1 to about 3 points, from about 1 to about 3 points, from about 1 to about 2.5 points, or from about 1 to about 1.5 points. Patients treated in accordance with the present invention can report a reduction in light touch evoked pain, as measured by the NPRS, of from about 1 to about 4 points, from about 1 to about 3.5 points, from about 1 to about 3 points, from about 1 to about 3.5 points, from about 1 to about 2 points, or from about 1 to about 1.5 points. Patients treated in accordance with the present invention can report a reduction in cold evoked pain, as measured by the NPRS, of from about 1 to about 3 points, from about 1 to about 3.5 points, from about 1 to about 2 points, or from about 1 to about 1.5 points.

Patients treated in accordance with the present invention can report significant pain reduction following treatment with capsaicin, as measured by the Short Form McGill Pain Questionnaire (SFMPQ). For example, patients treated in accordance with the present invention can report a reduction in continuous pain, as measured by the SFMPQ, of from about 5 to about 15 points, from about 7 to about 15 points, or from about 10 to about 15 points. Patients treated in accordance with the present invention can report a reduction in intermittent pain, as measured by the SFMPQ, of from about 5 to about 10 points, from about 6 to about 10 points, or from about 7 to about 9 points. Patients treated in accordance with the present invention can report a reduction in affective pain, as measured by the SFMPQ, of from about 1 to about 10 points, from about 2 to about 8 points, or from about 3 to about 7 points. Patients treated in accordance with the present invention can report a reduction in neuropathic pain, as measured by the SFMPQ, of from about 5 to about 20 points, from about 5 to about 15 points, or from about 5 to about 10 points. Patients treated in accordance with the present invention can report a reduction in overall pain, as measured by the SFMPQ, of from about 10 to about 50 points, from about 20 to about 40 points, or from about 25 to about 40 points.

Patients treated in accordance with the present invention can report significant pain reduction following treatment with capsaicin, as measured by the Patient Global Impression of Change (PGIC). For example, patients treated in accordance with the present invention can report a reduction in PGIC score of from about 0.5 to about 2, about 0.6 to about 2, or about 0.8 to about 1.6.

Patients treated in accordance with the present invention can display a reduction in neuropathy impairment score for the lower limbs (NIS-LL). For example, patients treated in accordance with the present invention can display a reduction in NIS-LL of from about 1 to about 10, from about 2 to about 8, or from about 3 to about 7.

According to certain embodiments, patients treated in accordance with the methods and products of the present invention may show nerve fiber regeneration, more particularly peripheral sensory nerve fiber regeneration. According to certain embodiments, patients treated in accordance with the methods and products of the present invention may show an increase in the density of nerve fibre terminals in a given area of skin.

Patients

The methods and kit of the present invention are provided for the treatment of patients who have previously received cancer chemotherapy (in particular neurotoxic cancer chemotherapy), and who are not currently receiving cancer chemotherapy. Such patients are typically human patients. A patient may be male or female. A patient may be of any age. Typically, a patient is an adult patient, for example a patient of from about 18 to about 80 years of age. A patient may be of any ethnic origin. A patient may have any body weight.

In some embodiments, the patient has not received cancer chemotherapy for at least about 3 months. The patient may not have received cancer chemotherapy for at least about 6 months, at least about 9 months, at least about 1 year, at least about 2 years, at least about 3 years, at least about 4 years, at least about 5 years, at least about 6 years, at least about 7 years, or at least about 8 years. For example, the patient may not have received cancer chemotherapy for at least about 2 years.

A patient for treatment according to the present invention may have experienced peripheral neuropathy induced by cancer chemotherapy (or suspected of having been induced by cancer chemotherapy) for more than about 3 months, more than about 6 months, more than about 9 months, more than about 1 year, more than about 2 years, more than about 3 years, more than about 4 years, more than about 5 years, more than about 6 years, more than about 7 years, or more than about 8 years.

In some embodiments, the patient is in remission from cancer. Partial remission refers to the reduction of the signs and symptoms of cancer, compared to baseline levels of the signs and symptoms observed previously in the same patient experiencing progressive cancer. For example, partial remission from cancer can refer to a reduction by more than about 10, 20, 30, 40 or 50% in the measurable parameters of cancer progression. Measureable parameters of cancer progression include those determined by physical examination, medical imaging, and/or biomarker levels in a blood or urine test. Full remission refers to the disappearance of the signs and symptoms of cancer. For example, full remission from cancer can refer to a return to normal, healthy levels of measurable parameters of cancer progression, such as those determined by physical examination, medical imaging, and/or biomarker levels in a blood or urine test. It will be appreciated that what is considered to constitute remission may differ from one cancer to another and from one patient to another.

In some embodiments, the patient has been in remission from cancer, whether partial or complete remission, for at least about 3 months before receiving treatment according to the present invention. The patient may have been in partial remission from cancer for at least about 3 months, at least about 6 months, at least about 9 months, at least about 1 year, at least about 2 years, at least about 3 years, at least about 4 years, at least about 5 years, at least about 6 years, at least about 7 years, or at least about 8 years. For example, the patient may have been in partial remission from cancer for at least about 3 months. The patient may have been in full remission from cancer for at least about 3 months, at least about 6 months, at least about 9 months, at least about 1 year, at least about 2 years, at least about 3 years, at least about 4 years, at least about 5 years, at least about 6 years, at least about 7 years, or at least about 8 years. For example, the patient may have been in full remission from cancer for at least about 3 months.

Patients for treatment according to the present invention may experience peripheral neuropathy induced by cancer chemotherapy of varying severity. For example, prior to receiving treatment according to the present invention, a patient may have been experiencing sufficiently severe symptoms of peripheral neuropathy to require treatment of those symptoms by pain medication. Examples of such pain medication include, but are not limited to: acetaminophen; gabapentinoids (including pregabalin and gabapentin); tricyclic anti-depressants; opioids; and other analgesic combinations.

Cancer Chemotherapy

Examples of cancer chemotherapy received by a patient include, but are not limited to, cancer chemotherapy for the treatment of one or more of: ovarian cancer; breast cancer; squamous cell cancer; lung cancer (including small-cell lung cancer and non-small cell lung cancer); adenocarcinoma of the lung; squamous carcinoma of the lung; cancer of the peritoneum; hepatocellular cancer; gastric or stomach cancer (including gastrointestinal cancer); pancreatic cancer; glioblastoma; cervical cancer; liver cancer; bladder cancer; hepatoma; colon cancer; colorectal cancer; endometrial or uterine carcinoma; salivary gland carcinoma; kidney or renal cancer; liver cancer; prostate cancer; vulval cancer; thyroid cancer; hepatic carcinoma; various types of cancer of the head and neck; B-cell lymphoma (including low grade/follicular non-Hodgkin's lymphoma (NHL); small lymphocytic NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's Macroglobulinemia; chronic lymphocytic leukemia; acute lymphoblastic leukemia; hairy cell leukemia; chronic myeloblastic leukemia; and post-transplant lymphoproliferative disorder.

In some embodiments, the cancer chemotherapy received by the patient comprises treatment by one or more neurotoxic chemotherapeutic agents. Examples of neurotoxic chemotherapeutic agents include, but are not limited to: taxanes such as paclitaxel (taxol) and docataxel; platinum-containing chemotherapeutic agents such as cisplatin, carboplatin and oxaliplatin; *vinca* alkaloids such as vincristine; cytabarine; ifosfamide; bortezomib; and methotrexate. In some embodiments, the cancer chemotherapy received by the patient comprises treatment by one or more platinum-containing chemotherapeutic agents. In some embodiments, the one or more neurotoxic chemotherapeutic agents are selected from one or more of: cisplatin, paclitaxel, docetaxel, vincristine, oxaliplatin, and bortezomib.

The cancer chemotherapy received by the patient may have involved treatment by a single cancer chemotherapy agent. The cancer chemotherapy received by the patient may have involved treatment by more than one cancer chemotherapy agent.

Factors determining the duration of cancer chemotherapy that was received by the patient include, but are not limited to: the type of cancer, the extent of cancer, the type(s) of cancer chemotherapy agent(s), the toxicity of the agent(s), and whether the patient and their physician decided to continue or discontinue chemotherapy. More than one different chemotherapy agent may have been received simultaneously. More than one different chemotherapeutic agent may have been received sequentially.

The patient may have received a single dose of cancer chemotherapy. The patient may have received more than one dose of cancer chemotherapy. One or more doses of the chemotherapy agent(s) may have been received over a period of time. For example, one or more doses may have been received in one or more cycles of chemotherapy over a period of time, such as one or more cycles that repeat on a weekly, bi-weekly, or monthly basis. For example, a patient may have received one, two, three, four, five, six or more cycles of chemotherapy. A patient may have received chemotherapy, whether continuously (i.e., in regular cycles of treatment) or sporadically, over a period of at least about 1 month, at least about 2 months, at least about 3 months, at least about 6 months, at least about 9 months, at least about 1 year, at least about 2 years, at least about 3 years, at least about 4 years, at least about 5 years, or more.

Kit Leaflet

The kit of the second aspect of the present invention comprises a cutaneous patch and a leaflet. The leaflet provides instructions for a method of treating peripheral neuropathy induced by cancer chemotherapy, comprising administering the cutaneous patch to one or more areas of the skin of a patient in need thereof, wherein the cutaneous patch is administered after the patient has received cancer chemotherapy, and wherein the patient is not currently receiving cancer chemotherapy. The leaflet may further provide instructions for a method of inducing regeneration of peripheral nerve fibres. The cutaneous patch of the kit of the second aspect of the invention is a cutaneous patch containing about 500 to about 700 μg of capsaicin or a capsaicinoid per cm$^2$ of patch.

In certain embodiments, the method of the first aspect of the invention or the method of the third aspect of the invention may include use of a kit as according to the second aspect of the invention. Thus, the instructions in the leaflet can include instructions for carrying out a method according to the first aspect of the invention, which is directed to treating peripheral neuropathy induced by cancer chemotherapy. The instructions in the leaflet can additionally include instructions for carrying out a method according to the third aspect of the invention, which is directed to stimulating the regeneration of peripheral sensory nerve fibers. The instructions in the leaflet can include both instructions for carrying out the method according to the first aspect of the invention, and for carrying out the method according to the third aspect of the invention.

In certain embodiments, a kit according to the second aspect of the invention may additionally comprise one or more items selected from cleansing gel, gauze, soap and personal protective equipment, such as gloves. It will be understood that a leaflet included in the kit may therefore provide instructions describing how to use one or more items selected from cleansing gel, gauze, soap and personal protective equipment. For example, the leaflet may provide instructions describing how to use one or more items selected from cleansing gel, gauze, soap and personal protective equipment in accordance with the method of the first or third aspect of the invention.

The leaflet may provide instructions for administering capsaicin or a capsaicinoid in a particular dosage using the cutaneous patch of the second aspect of the invention, for example a dosage provided herein in accordance with the method of the first aspect of the invention or the method of the third aspect of the invention. The leaflet may provide instructions on how often to repeat treatment using the cutaneous patch, such as how treatment can be repeated at particular time intervals, for example at time intervals provided herein in accordance with the method of the first or third aspect of the invention.

The leaflet may provide instructions for administering capsaicin or a capsaicinoid to a patient having one or more particular characteristics, as described herein. For example, the leaflet may provide instructions for administering capsaicin or a capsaicinoid to a patient who has not received cancer chemotherapy for at least a specified length of time, for example a length of time described herein. The leaflet may provide instructions for administering capsaicin or a capsaicinoid to a patient who has experienced peripheral neuropathy induced by cancer chemotherapy (or suspected of having been induced by cancer chemotherapy) for more than a specified length of time, for example a length of time described herein. The leaflet may provide instructions for administering capsaicin or a capsaicinoid to a patient who has been in remission from cancer, whether partial or complete remission, for at least a specified length of time, for example a length of time described herein.

It will be appreciated that the one or more areas of skin to which the cutaneous patch is administered can differ from patient to patient, depending on their symptoms and signs of peripheral neuropathy and the extent of the peripheral neuropathy across the body surface. The one or more areas of skin to which capsaicin or a capsaicinoid is administered can be one or more areas of skin that exhibit symptoms and/or signs of peripheral neuropathy induced by chemotherapy. Therefore, the instructions of the leaflet may include instructions on how to determine the one or more areas of skin for exposure to the cutaneous patch, for example instructions describing how to determine the one or more areas of skin by touching different areas of skin to determine whether each area of the skin has symptoms. Additionally or alternatively, the instructions may describe how to trace that information directly onto the skin of the patient, using for example an ink pen to mark the skin. Additionally or alternatively, the instructions may describe how to obtain more sensitive, more accurate, or more objective information as to the extent of the peripheral neuropathy, by using neurophysiological testing, whereby a nerve conduction device is used to assess nerve fibre function.

The leaflet may provide instructions that warn the user about certain hazards associated with using the cutaneous patch. For example, the leaflet may state that hairs in the one or more areas of skin should not normally be shaved (in order to avoid breaking the skin) but should instead be clipped, before gently washing the treatment area(s) with soap and water, then drying the area(s). The instructions may warn the user that, for reasons of safety, the cutaneous patch should not normally be administered to the skin of, or near, the eyes. Likewise, the cutaneous patch should not normally be administered to mucous membranes. The instructions may warn the user that the cutaneous patch should not normally be administered to the skin of the head, and in particular the cutaneous patch should not normally be administered to the skin of the face. The instructions may warn the user that the cutaneous patch should not normally be administered to broken, irritated or otherwise sensitive areas of skin, for example the skin of the anogenital regions of the body. The instructions may advise a first-time user to test the cutaneous patch initially on a small area of skin, and for a short period of time, before proceeding to use the cutaneous patch for treatment, for example proceeding to use the cutaneous patch according to the method of the first or third aspect of the invention.

Whilst the present invention has been described and illustrated with reference to particular embodiments, it will be appreciated by those of ordinary skill in the art that the invention lends itself to many different variations not specifically illustrated herein.

EXAMPLES

Study Design

Figure 1:
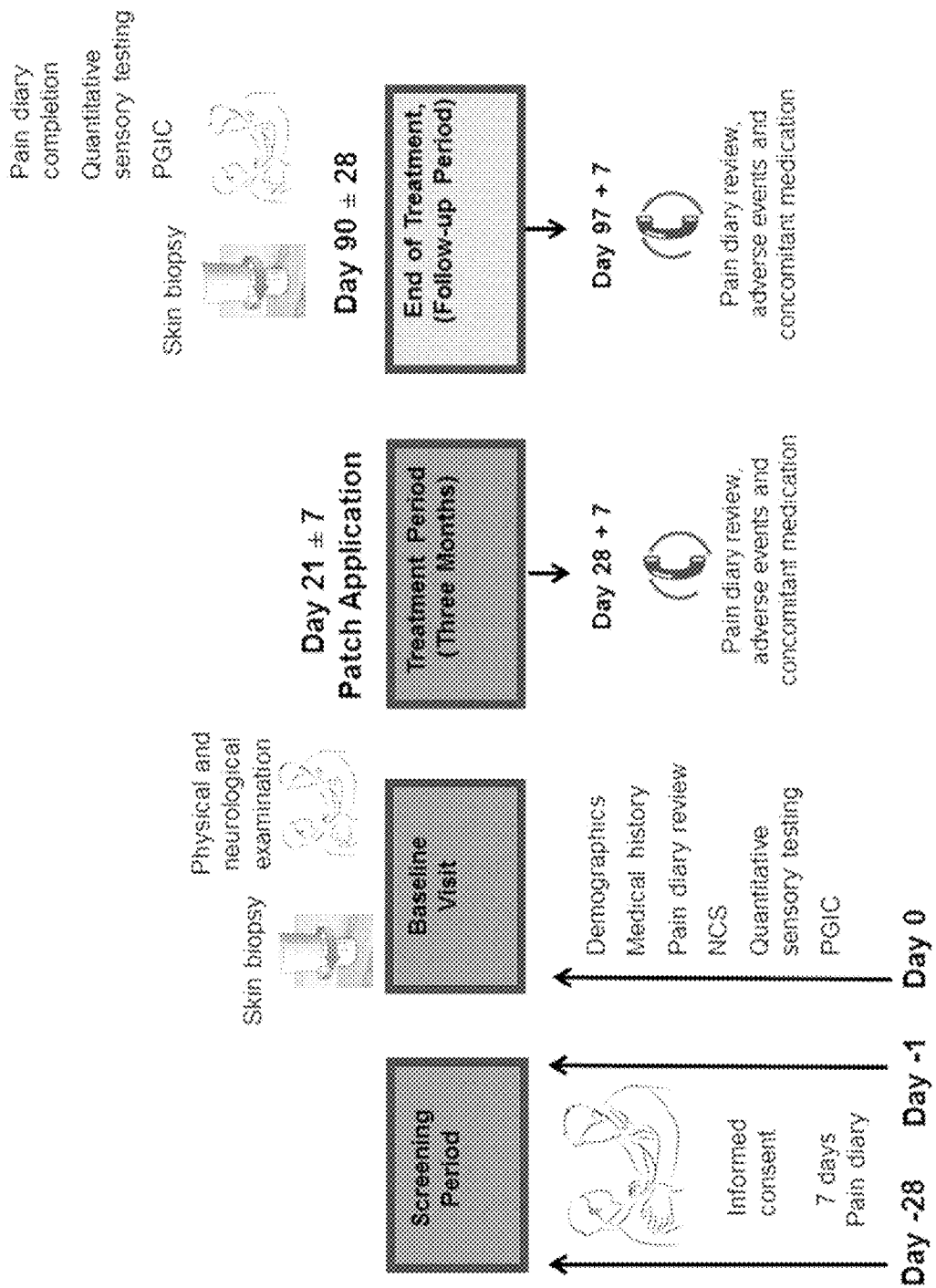
FIG. 1 shows a study flow diagram setting out the steps of a study as described herein. Abbreviations in FIG. 1: NCS: Nerve conduction study, PGIC: Patient Global Impression of Change.

A single center, open-label, longitudinal study, with Capsaicin 8% Patch treatment as licensed, was conducted in patients who attended the Peripheral Neuropathy Unit, Imperial College London, based at Hammersmith Hospital, Imperial College Healthcare NHS Trust (Anand et al., *J Pain Res* 2019, 12: 2039-2052, incorporated herein by reference in its entirety). The study was approved by the London Fulham Research Ethics Committee (Ethics reference number: 12/LO/0895). The study involved hospital visits and telephone calls, as shown in FIG. 1. Patients attended the hospital unit for study visits 1 to 3, and the application of the Capsaicin 8% Patches was carried out in the hospital as previously described in detail, with illustrations (Privitera et al., *J Pain Res* 2017, 10: 1623-1634, incorporated herein by reference in its entirety). The Capsaicin 8% Patches covered the feet and distal calf, including the region of the pre-treatment baseline skin biopsies, after they had fully healed. All patients had a total number of 4 patches, 2 for each foot.

Participants

Patients with painful CIPN for at least 3 months prior to enrolment, and aged between 18-80 years, were eligible for inclusion in the study. 16 patients with different types of cancer, who had received chemotherapy (mainly platinum, taxane, and proteasome inhibitor compounds) and developed symptoms of CIPN, were enrolled. Patients Demographic and characteristics are outlined in Table 1.

TABLE 1

Patients' demographics and clinical characteristics

| Patient demographics | |
|---|---|
| Mean Age [years, range] | 64 (45-79) |
| Number of patients | 16 |
| Number of male patients (%) | 8 (50%) |
| Ethnic Origin: | |
| Asian or Asian British | 25.0% |
| Caucasian | 68.0% |
| Other | 7.0% |

TABLE 1-continued

Patients' demographics and clinical characteristics

| Clinical Characteristics | |
|---|---|
| Mean Duration of CIPN [years, range] | 2.5 (5 month-8 years) |
| Pain level at baseline [NPRS, mean (SEM)] | 6.6 (0.43) |
| Number of patients taking pain medications at baseline | 12 (75%) |
| Acetaminophen (Paracetamol) | 2 |
| Gabapentinoids (Pregabalin and Gabapentin) | 4 |
| Tricyclic anti-depressants/SNRI | 1 |
| Opioids | 4 |
| Other analgesic combinations | 1 |
| Patient Cancer types: | |
| Cancer Colon | 7 |
| Multiple Myeloma | 6 |
| Lung Cancer | 1 |
| Cancer Ovary | 2 |
| Patient Chemotherapy types: | |
| Bortezomib | 6 |
| Platinum/Taxane or both | 10 |

Abbreviations: CIPN, Chemotherapy-induced peripheral neuropathy; SEM, Standard error of the mean; NPRS, Numerical Pain Rating Scale.

All patients fulfilled the criteria for neuropathy outlined by the National Cancer Institute of Canada Common Toxicity Criteria (NCIC-CTC), including pain and hypersensitivity. Patients were considered suitable for the study if their symptoms had been stable on their prescribed medical treatment for 8 weeks prior to enrolment. Patients described symptoms in their lower limbs, most commonly numbness, pins, and needles, tingling and burning pain or discomfort. All patients reported pain in their feet; most were taking treatment for pain at the start of the study (gabapentin, pregabalin, amitriptyline, duloxetine, tramadol, oxycodone, or a combination of these).

Clinical Symptoms and Pain Assessment Scales

Patients were given a study diary to complete starting on the day of screening and continuing for the next 7 days. The diary collected numerical pain rating scores (NPRS) twice daily. An 11-point numerical rating scale (NRPS), with the 0 point being "no pain" and the 10 point being "pain as bad as you can imagine," was used to describe "pain on average in the last 24 hours" for spontaneous and evoked pain. After 7 days of completing this diary, a member of the study team contacted the patients by telephone and averaged the result of their NPRS to determine their eligibility for the study. Only patients with average pain intensity equal or greater than 4/10 on the NPRS for spontaneous pain were eligible to participate further in the study and were advised to continue with the study diary until the end-of-study follow up visit. Symptoms were also assessed using the Short Form McGill Pain Questionnaire (SF-MPQ-2) (Melzack, The short-form McGill Pain Questionnaire, *Pain.* 1987, 30(2):191-197, incorporated herein by reference in its entirety). The standard Patient Global Impression of Change (PGIC) was recorded.

Clinical Examination and Assessment of Neuropathy

Clinical examination and tests were performed to confirm that patients had a predominantly sensory, length-dependent neuropathy. The Neuropathy Impairment Score Lower Limbs (NIS-LL) was recorded (Bril V. NIS-LL: the primary measurement scale for clinical trial endpoints in diabetic peripheral neuropathy. *Eur Neurol.* 1999, 41 Suppl. 1:8-13, incorporated herein by reference in its entirety).

Nerve conduction studies were performed once at the start of the study for all patients. Nerve conduction studies of the common peroneal (including F wave studies) and sural nerves in the right leg were performed in a standardized manner by the same examiner on a Medtronic Keypoint electromyogram (Medtronic, Minneapolis, Minn., USA). Sural antidromic sensory action potentials of <5 µV amplitude and 40 m/s conduction velocity were considered abnormal, and common peroneal nerve (compound muscle action potential from extensor digitorum brevis) values <3 mV amplitude, and 40 m/s conduction velocity were considered abnormal. 70 An F-wave latency >60 ms was considered abnormal.

Most patients (66%) had at least one abnormality on the nerve conduction study, 11% had both motor and sensory abnormality. F-waves were absent in 1 patient. The mean±SEM (range) for the peroneal motor action potential was 3.8±0.5 (1.2-6.3) µV and for the peroneal conduction velocity was 46±1.4 (40-56.8) m/s. The mean±SEM (range) for the sural sensory action potential was 6.8±1.4 (0.0-16) µV, and for the sural nerve velocity was 44.1±6.3 (0.0-67) m/s.

Quantitative Sensory Testing (QST)

For quantitative sensory testing (QST), thresholds for light touch were measured using Semmes-Weinstein hairs (made by A. Ainsworth, University College London, UK), No. 1 (0.0174 g) to No 20 (263.0 g). The number of the hair with the lowest force reliably detected by the patient on the dorsum of the toe was recorded. Values >No. 3 monofilament (0.0479 g) were considered abnormal (Atherton et al., *BMC Neurol.* 2007, 7:21, incorporated herein by reference in its entirety). Vibration perception thresholds were measured using a biothesiometer (Biomedical Instrument Company, Newbury, Ohio, USA) placed on the metatarsophalangeal joint of the big toe. Three ascending and three descending trials were carried out, and the mean value obtained. Values >12 V were considered abnormal (Coppini et al., *J Clin Neurosci.* 2001, 8(6):520-524, incorporated herein by reference in its entirety).

Thermal perception thresholds were performed as described in previous publications (Wellmer et al., *J Peripher Nerv Syst.* 2001, 6(4):204-210; Anand et al., *Nat Med.* 1996, 2(6):703-707, each of which is incorporated herein by reference in its entirety) using the TSA II-Neuro-Sensory Analyzer (Medoc, Ramat Yishai, Israel). A 30 mm×30 mm thermode was used and thermal thresholds determined in the soles of the feet (under the instep), right lateral calf and palms of the hands (thenar eminence) for warm perception, cool perception, heat pain and cold pain from a baseline temperature of 32° C., with a change in temperature of 1° C./s. The mean of three consecutive tests for each modality was recorded. Values >6.4° C. for warm sensation, >2.3° C. for cool sensation and >10.4° C. for heat pain, were considered abnormal (Atherton et al., *BMC Neurol.* 2007, 7:21; 72; Wellmer et al., *J Peripher Nerv Syst.* 2001, 6(4):204-210; Anand et al., *Nat Med.* 1996, 2(6):703-707, each of which is incorporated herein by reference in its entirety).

Calf Skin Biopsy and Immunohistochemistry

Two 3.5-mm diameter skin punch biopsies were collected under local anesthesia from the distal lateral calf of 16 patients with CIPN on visit 1 before Capsaicin 8% Patch application, and repeated 3 months after patch application. The immunohistochemical methods and antibodies used here had been reported previously (Rage et al., *Clin Neurophysiol.* 2010, 121(8):1256-1266; Gopinath et al., *BMC Women's Health.* 2005, 5(1):2; Facer et al., *Brain.* 1998, 121 (Pt 12): 2239-2247, each of which is incorporated herein by reference in its entirety). One of the two skin biopsies was snap frozen and stored at −70° C., and the other immersed in fixative (modified Zamboni's fluid—2% formalin; 0.01 M phosphate buffer; 15% saturated picric acid (pH 7.2), then washed in phosphate buffered saline (PBS; 0.1 M phosphate; 0.9% w/v saline; pH 7.3) containing 15% w/v sucrose for an hour, before snap freezing in optimum cutting tissue embedding medium (Tissue-Tek OCT, RA Lamb Ltd, Eastbourne, U.K.). Frozen sections (15 µm thickness) were collected onto poly-L-lysine (Sigma, Poole, UK) coated glass slides and post-fixed in freshly prepared, 4% w/v paraformaldehyde in 0.15M phosphate buffered saline (PBS) for 30 min. Sections of pre-fixed tissue were collected in the same way and allowed to air dry for markers. Endogenous peroxidase was blocked by incubation in industrial methylated spirit containing 0.3% w/v hydrogen peroxide for 30 minutes for both post- and pre- (Zamboni) fixed sections. After rehydration, appropriately processed sections were incubated overnight with primary antibodies (n=16 biopsies, unless stated otherwise, as tissue was not enough to study all markers in some biopsies). The antibodies were to the structural nerve marker PGP 9.5 (Rabbit, RA95/06, 1:40,000; Ultraclone, Isle of Wight, UK), the heat and capsaicin receptor transient receptor potential vanilloid 1 TRPV1 (Rabbit, C22, 1:10,000; GlaxoSmithKline, Harlow, UK), the human sensory neuron-specific receptor SNSR, marker of IB-4 nociceptor subset (Rabbit, 1:15,000; gift from Astra Zeneca, Montreal, Canada) nerve regeneration marker, growth associated protein GAP-43 (G9264, Mouse, 7B10, 1:80,000; Sigma, Poole, UK), recombinant human Nerve Growth Factor (Genentech Inc, San Francisco, USA, Rabbit, 12756/71, 1:2000), NT3 (Rabbit, C/845 No 883, 1:50,000, Amgen, Thousand Oaks, USA) epidermal Langerhans cells marker S-100 (Rabbit, Z311, 1:40,000, Dakocytomation, Dako UK, Ltd, Cambridge, UK). Sites of primary antibody attachment were revealed using nickel-enhanced, avidin-biotin peroxidase (ABC—Vector Laboratories, Peterborough, UK) as previously described ((Ragé et al., *Clin Neurophysiol.* 2010, 121(8):1256-1266; Gopinath et al., *BMC Women's Health.* 2005, 5(1):2; Facer et al., *Brain.* 1998, 121 (Pt 12): 2239-2247, each of which is incorporated herein by reference in its entirety). Sections were counterstained for nuclei in 0.1% w/v aqueous neutral red, air dried and mounted in xylene-based mountant (DPX; BDH/Merck, Poole, UK), prior to analysis. Negative controls included omission of primary antibodies or their replacement with pre-immune serum.

Nerve fibers were counted along the length of four nonconsecutive sections. The length of epithelium in each counted section was measured using computerized microscopy software (Olympus ANALYSIS 5.0 Soft, Olympus UK, Southend, Essex, UK) and results expressed as fibers/mm length of the section. Sub-epidermal nerve immunereactivity obtained as a percentage (% area) measured by image analysis where digital photomicrographs were captured via video link to an Olympus BX50 microscope. The grey-shade detection threshold was set at a constant level to allow detection of positive immuno-staining and the area of highlighted immuno-reactivity was expressed as a percentage (% area) of the field scanned. Images were captured (×40 objective magnification) along the entire length, and the mean values were used for statistical analysis. Quantification was performed by two independent blinded observers, and there was no significant difference between observers.

Validation and justification of these methods, including for PGP9.5 Intra-epidermal nerve fiber (IENF) density in 50 μm vs. 15 μm thickness sections, have been published previously (Van Acker et al., *BMC Res Notes* 2016, 9:280. DOI 10.1186/s13104-016-2085-4; Anand P et al., *Front. Neurol.*, 2017 8:514. DOI: 10.3389/fneur.2017.00514, both incorporated herein by reference in their entirety).

Statistical Analysis

Data were analyzed using GraphPad Prism version 5.0 for Windows (GraphPad Prism Software, San Diego, Calif., USA). The statistical test used was the paired two-tailed Mann-Whitney test. Values were compared before and after the treatment with Capsaicin 8% Patch. For all statistical tests, p values <0.05 were considered significant.

Results

Neuropathy Impairment Score Lower Limbs (NIS-LL) showed a significant improvement after treatment with the Capsaicin 8% Patch (p=0.01), with a reduction of the mean score ±SEM of 1.875±0.40 (Table 2).

TABLE 2

Results before and after Capsaicin 8% Patch: Spontaneous pain (NPRS), Short Form McGill Pain Questionnaire, Patient Global Impression of Change, Quantitative Sensory Testing, and Contact Heat Evoked Potentials.

Numerical Pain Rating Scale (NPRS) [mean ± SEM]

|  | Pre patch application | Post patch application | p-value |
| --- | --- | --- | --- |
| Spontaneous pain | 6.6 ± 0.4 | 5.3 ± 0.5 | 0.01 |
| Light touch evoked pain | 4.8 ± 0.8 | 2.6 ± 0.7 | 0.02 |
| Cold evoked pain | 4.0 ± 0.8 | 2.6 ± 0.8 | 0.03 |

Short Form McGill pain Questionnaire (SFMPQ) [mean ± SEM]

|  | Pre patch application | Post patch application | p-value |
| --- | --- | --- | --- |
| Continuous pain | 27.9 ± 3.6 | 14.9 ± 2.9 | 0.001 |
| Intermittent pain | 21.2 ± 3.8 | 14.0 ± 3.1 | ns |
| Affective pain | 9.5 ± 2.8 | 9.4 ± 2.4 | ns |
| Neuropathic pain | 30.5 ± 3.3 | 19.5 ± 2.6 | 0.0007 |
| Overall pain | 83.6 ± 12.3 | 53.5 ± 8.7 | 0.003 |

Patient Global Impression of Change (PGIC) [mean ± SEM]

|  | Pre patch application | Post patch application | p-value |
| --- | --- | --- | --- |
| PGIC score | 4.2 ± 0.2 | 2.8 ± 0.3 | 0.003 |

Quantitative Sensory Testing (QST) [mean ± SEM]

|  | Pre patch application | Post patch application | p-value |
| --- | --- | --- | --- |
| Cool Threshold (° C.) | 20.4 ± 2.1 | 20.7 ± 1.7 | ns |
| Warm Threshold (° C.) | 44.3 ± 1.2 | 43.9 ± 0.9 | ns |
| Cold Pain Threshold (° C.) | 9.6 ± 2.1 | 10.4 ± 2.4 | ns |
| Heat Pain Threshold (° C.) | 47.9 ± 0.7 | 48.2 ± 0.6 | ns |
| Vibration Threshold (V) | 33.6 ± 3.4 | 28.7 ± 3.0 | ns |
| Monofilament Threshold (g) | 34.9 ± 22.2 | 2.3 ± 1.4 | ns |

Neuropathy Impairment Score Lower Limbs (NIS-LL) [mean ± SEM]

|  | Pre patch application | Post patch application | p-value |
| --- | --- | --- | --- |
| NIS-LL Score | 10.5 ± 1.2 | 8.6 ± 0.8 | 0.01 |

Abbreviations: SEM, Standard error of the mean; NPRS, Numerical Pain Rating Scale; ns, not significant; PGIC, Patient Global Impression of Change; QST, Quantitative Sensory Testing; NIS-LL, Neuropathy Impairment Score Lower Limbs; ° C.: Celsius degree; V: Volt; g: gram.

Pain Scores and Questionnaires

There was a significant reduction in the average (±SEM) daily NPRS for spontaneous pain, −1.271 (±0.077), p=0.02, three months after Capsaicin 8% Patch application (baseline week vs. week 12 after patch application). There was also a significant reduction in scores for pain evoked by touch −1.823 (±0.07), p=0.03, and cold −1.456 (±0.06), p=0.03 (see Table 2).

Short-Form McGill Pain Questionnaire (SF-MPQ-2) showed a significant reduction in the continuous (−13.0±0.66, p=0.001) and neuropathic (−11.7±0.72, p=0.0007) pain scores. There was no significant difference in the intermittent and affective pain scores.

Patient Global Impression of Change (PGIC) showed significant improvement, p=0.0029 (see Table 2).

Quantitative Sensory Testing

All patients showed abnormalities on QST pre-treatment compared to normal values reported previously (Narayanaswamy et al., *J Clin Neurosci.* 2012, 19(11):1490-1496, incorporated herein by reference in its entirety) in accord with other laboratories. There was no significant change after treatment (p >0.05, see Table 2).

Immunohistochemistry

Figure 2:
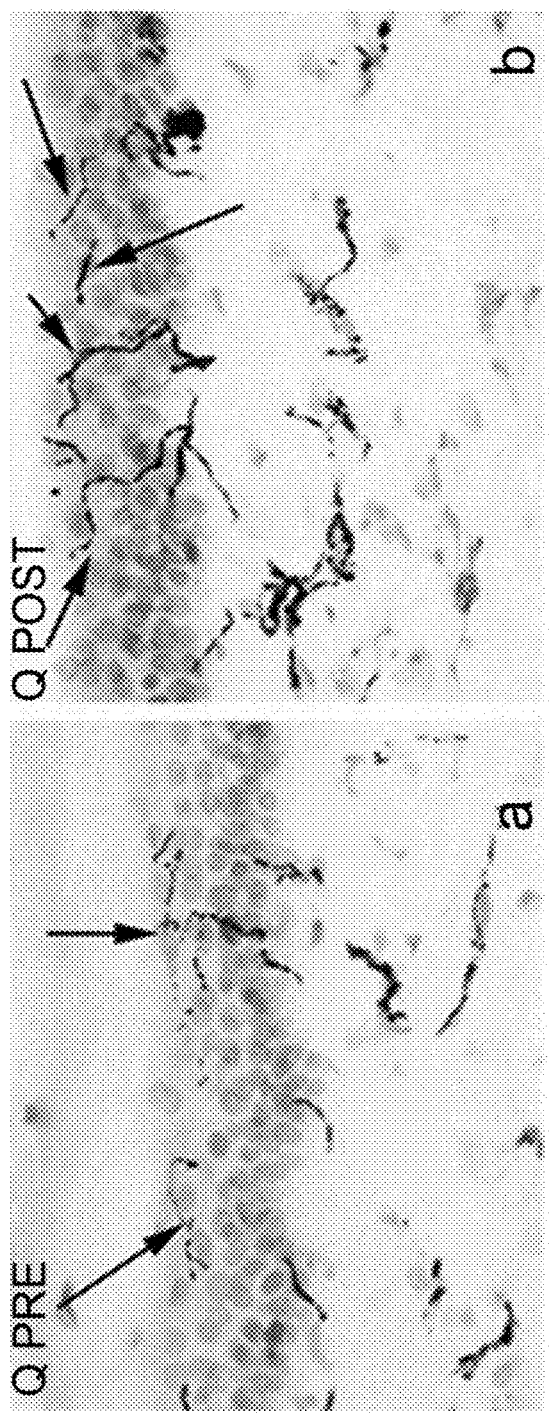
FIG. 2 shows immunohistochemistry in skin biopsies for PGP9.5, before and after Capsaicin 8% Patch treatment. Shown in (a) are intra-epidermal nerve fibers (arrowed) and sub-epidermal nerve fibers at the baseline visit (Q PRE), magnification ×40. Shown in (b) are intra-epidermal nerve fibers (arrowed) and sub-epidermal nerve fibers after Capsaicin 8% Patch treatment (Q POST), magnification ×40.
Figure 2:
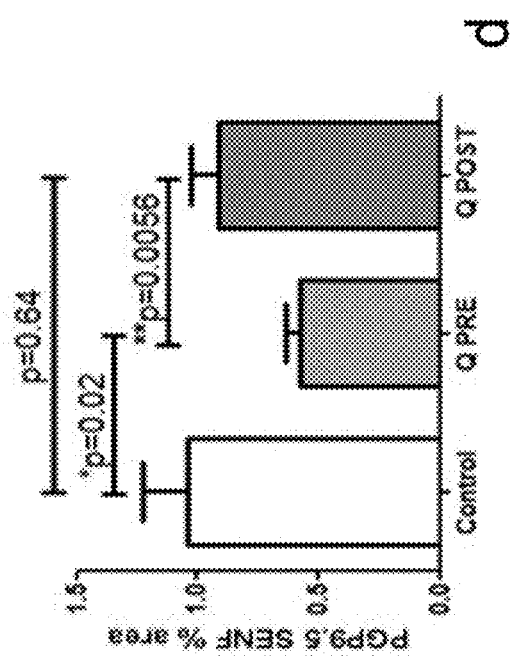
Figure 2:
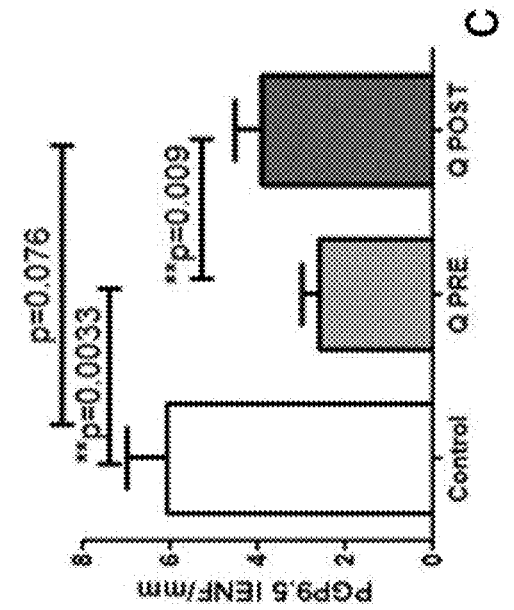

Skin biopsies at baseline showed fewer PGP9.5-immunoreactive intra-epidermal nerve fibers (IENF) counts than controls (Atherton et al., *BMC Neurol.* 2007, 7:21, incorporated herein by reference in its entirety). There was a significant increase in PGP9.5 IENF fibers after Capsaicin 8% Patch treatment patients (p=0.009, FIG. 2), and in subepithelial nerve fibers (SENF), (p=0.0056). There was also a significant increase in TRPV1 IENF fibers (p=0.027, FIG. 3), and in TRPV1 SENF (p=0.001). PGP9.5 and TRPV1 IENF and SENF were not statistically different from controls following capsaicin 8% treatment, unlike at baseline. There were no significant differences between Sensory Neuron-specific Receptors (SNSR) IENF and SNSR SENF (p=0.7 and 0.18 respectively; FIG. 4). GAP-43 immunoreactive IENF were significantly more abundant after Capsaicin 8% Patch treatment (p=0.024), and also GAP-43 SENF (p=0.004), compared to baseline (FIG. 5). GAP-43 IENF were significantly increased following Capsaicin 8% Patch treatment compared to controls (p=0.039).

NGF antibodies labeled basal keratinocytes which express NGF which normally helps maintain the IENF (Anand et al, *Nat Med.* 1996, 2(6): 703-707; Anand et al., *Neuroreport.* 1997, 8(8):1935-1938; Anand, *Prog Brain Res.* 2004, 146:477-492; Yiangou et al., *J Peripher Nerv Syst.* 2002 7(3):190-197, each of which is incorporated herein by reference in its entirety) (FIG. 6). In this study, there was a decrease of NGF in basal keratinocytes compared to controls at baseline (p=0.012), but an increase towards normal values after treatment with Capsaicin 8% Patch (p=0.0035, FIG. 6); further, this reversal appeared to restore levels towards normal values compared to controls (p=0.44, FIG. 6). In both control and CIPN subjects, Neurotrophin 3 (NT3) antibodies labeled suprabasal keratinocytes (FIG. 7). There was a significant increase in NT3 levels in CIPN patients before treatment compared to control subjects (p=0.0348 (FIG. 7), which was abolished after treatment with Capsaicin 8% Patch (p=0.1778, FIG. 7); this decrease of NT3 was significant (p=0.009, FIG. 7). S100 antibody labeled Langerhans cells (LCs) (FIG. 8). These were decreased, towards normal levels, after Capsaicin 8% Patch treatment (p=0.002, FIG. 8).

Discussion

Chemotherapy-induced peripheral neuropathy with associated chronic pain has a major impact on the quality of life of cancer patients, including those in remission from cancer.

Current symptomatic treatments used for neuropathic pain have limited efficacy with significant side-effects, and there are no preventive measures for development of CIPN, or amelioration of established painful CIPN.

In the study described herein, CIPN patients reported significant pain reduction following a single 30-minute treatment with the Capsaicin 8% Patch—in spontaneous pain, touch-evoked pain and cold-evoked pain. Their Short-Form McGill questionnaire showed a reduction in neuropathic, continuous and overall pain scores; Patient Global Impression of Change also showed improvement. The effect-size on pain relief by Capsaicin 8% Patch was similar to that for chronic neuropathic pain caused by other conditions, and as reported recently in two open label treatment studies for painful CIPN (Filipczak-Bryniarska et al, *Med Oncol* 2017, 34(9):162; Le Marec et al., *J. Clin. Oncol.* 2017, Vol 34, No 15 suppl. J Clin. Oncol.). QST remained unchanged, and there were no systemic side-effects, as in previous clinical trials.

Further key findings in the present study were the changes observed in skin biopsy markers. The baseline skin biopsies showed loss of intra-epidermal nerve fibers (IENF), as in painful small fibre neuropathy caused by several other conditions. Post-patch application skin biopsies showed a significant increase towards normalization of intra-epidermal and sub-epidermal nerve fibers for the pain-neuronal structural marker PGP9.5, capsaicin and heat receptor TRPV1, and regenerating nerve fibers with the selective marker GAP43. PGP9.5 IENF and SENF, and TRPV1 IENF were not statistically different from controls following capsaicin 8% treatment, unlike at baseline, when they were significantly decreased. GAP-43 IENF were significantly increased after Capsaicin 8% Patch treatment, compared to baseline and controls. GAP-43 SENF were significantly increased following Capsaicin 8% Patch treatment compared to baseline, while decreased at baseline compared to controls. These findings suggest significant regeneration of these cutaneous nerve fiber terminals. Epidermal Nerve Growth Factor (NGF), Neurotrophin-3 (NT-3), and Langerhans cells were also changed towards "normalization" post-patch application, which can enable healthier interactions between nerve fibres and their targets in skin.

Capsaicin 8% Patch is a topical formulation for the treatment of peripheral neuropathic pain; its mechanism of action has been reviewed in detail (Anand et al., *Br J Anaesth.* 2011, 107(4):490-502). In brief, capsaicin is the pungent "hot" ingredient in chili peppers, a natural selective agonist of the vanilloid receptor TRPV1. It is released rapidly from the Capsaicin 8% Patch and leads to an overstimulation of skin nociceptors—they are 'defunctionalized' acutely, and are no longer able to respond to the range of stimuli that normally cause pain in patients with peripheral neuropathic pain (Anand et al., *Br J Anaesth.* 2011, 107(4):490-502). The defunctionalization occurs in nociceptor cutaneous terminals, as the patch has an effect on the mitochondrial function to the dermis, with a concentration gradient. A single application of Capsaicin 8% Patch can provide pain relief for up to 3 months or more—however, the effect of the patch is reversible, and nerve fiber terminals usually regenerate, thus some patients require 3-monthly patch applications for pain relief.

This study shows that a single application of Capsaicin 8% Patch, by "pruning" the abnormal nerve fibers, can induce nerve regeneration and restoration of the nerve fiber phenotype in skin biopsies, for post-chemotherapy patients. After a course of chemotherapy (which affects both nerves and target skin cells e.g. keratinocytes) has ended, the nerve fiber terminals are no longer hindered by the presence of chemotherapeutic agents from regenerating "normally". The Capsaicin 8% Patch therefore not only provides significant pain relief in CIPN, it can also lead to regeneration and restoration of sensory nerve fibers i.e. promoting healing.

The inverse correlation between NGF and NT-3 levels observed before and after treatment with Capsaicin 8% Patch, suggests that key epidermal neurotrophins can play a role in painful peripheral neuropathies. Decreased epidermal expression and level of NGF (e.g. induced by cancer chemotherapy) which is toxic to epidermal keratinocytes expressing NGF, may lead to reduced IENF. The increased level of NT-3 observed at baseline in this study can be attributed to a possible compensatory mechanism.

The potential role of Langerhans cells in painful CIPN has been described (Siau et al., *Exp Neurol.* 2006, 201(2): 507-514) and their changes following treatment with Capsaicin 8% Patch towards normalization in our study suggests a contribution in pain relief, or secondary effects. It appears, in light of the present study, that the Capsaicin 8% Patch can lead to regeneration and restoration of sensory nerve fibers.

CONCLUSION

This study shows that capsaicin can induce nerve fiber regeneration. The present inventors have found that capsaicin-induced cutaneous nerve terminal axotomy triggers nerve fiber regeneration, which can provide significant relief in both painful and non-painful CIPN.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A method of treating peripheral neuropathy induced by cancer chemotherapy, comprising administering topically to one or more areas of the skin capsaicin or a capsaicinoid or a TRPV1 agonist to a patient in need thereof, wherein capsaicin is administered in an amount effective to induce cutaneous nerve terminal axotomy followed by nerve terminal regeneration, and wherein the capsaicin or capsaicinoid is administered after the patient has received cancer chemotherapy, and wherein the patient is not currently receiving cancer chemotherapy.

2. The method according to claim 1, wherein the capsaicin or capsaicinoid or TRPV1 agonist is capsaicin.

3. The method according to claim 2, wherein about 500 to about 700 μg of capsaicin per $cm^2$ of skin is administered to the one or more areas of the skin of the patient.

4. The method according to claim 2, wherein the capsaicin is administered in a cutaneous patch.

5. The method according to claim 2, wherein administering capsaicin topically comprises administering Capsaicin 8% Patch to the one or more areas of the skin of the patient.

6. The method according to claim 2, wherein capsaicin is administered topically to one or more areas of the skin of the patient for a period of about 30 minutes to about 60 minutes.

7. The method according to claim 2, wherein the patient is in remission from cancer.

8. The method according to claim 2, wherein the patient has not received cancer chemotherapy for at least about 3 months.

9. The method according to claim 2, wherein the cancer chemotherapy received by the patient comprises treatment by one or more platinum-containing chemotherapeutic agents.

10. The method according to claim 2, wherein the cancer chemotherapy received by the patient comprises treatment by one or more neurotoxic chemotherapeutic agents.

11. The method according to claim 10, wherein the one or more neurotoxic chemotherapeutic agents are selected from one or more of: cisplatin, paclitaxel, docetaxel, vincristine, oxaliplatin, and bortezomib.

12. The method according to claim 2, wherein the peripheral neuropathy includes painful peripheral neuropathy and/or non-painful peripheral neuropathy.

13. The method according to claim 2, wherein the symptoms of peripheral neuropathy comprise one or more of painful shooting sensations, burning pain, sensations of numbness, loss of balance, and non-painful spontaneous tingling.

14. A method of stimulating cutaneous nerve terminal axotomy followed by the regeneration of peripheral sensory nerve fibers, comprising administering capsaicin or a capsaicinoid or a TRPV1 agonist to a patient in need thereof, wherein the capsaicin is administered in an amount effective to induce cutaneous nerve terminal axotomy, and wherein the capsaicin or capsaicinoid or TRPV1 agonist is administered after the patient has received cancer chemotherapy, and wherein the patient is not currently receiving cancer chemotherapy.

15. The method according to claim 2, wherein the capsaicin is administered as the sole active ingredient.

16. The method according to claim 14, wherein the capsaicin is administered as the sole active ingredient.

17. The method of claim 1, wherein said administering of the capsaicin or the capsaicinoid or the TRPV1 agonist occurs only after said cancer chemotherapy is completed.

18. The method of claim 14, wherein said administering of the capsaicin or the capsaicinoid or the TRPV1 agonist occurs only after said cancer chemotherapy is completed.

19. The method of claim 2, wherein said administering of the capsaicin occurs only after said cancer chemotherapy is completed.

20. The method of claim 14, wherein the capsaicin or capsaicinoid or TRPV1 agonist is capsaicin, and said administering of the capsaicin occurs only after said cancer chemotherapy is completed.

* * * * *